(12) United States Patent
Clauson et al.

(10) Patent No.: US 11,723,802 B2
(45) Date of Patent: Aug. 15, 2023

(54) DEVICES AND METHODS FOR OCULAR SURGERY

(71) Applicant: Carl Zeiss Meditec Cataract Technology Inc., Reno, NV (US)

(72) Inventors: Luke W. Clauson, Reno, NV (US); Scott Chamness, Reno, NV (US); Michael Schaller, Reno, NV (US)

(73) Assignee: Carl Zeiss Meditec Cataract Technology Inc., Reno, NV (US)

( * ) Notice: Subject to any disclaimer, the term of this patent is extended or adjusted under 35 U.S.C. 154(b) by 674 days.

(21) Appl. No.: 16/811,786

(22) Filed: Mar. 6, 2020

(65) Prior Publication Data

US 2020/0306083 A1    Oct. 1, 2020

Related U.S. Application Data

(63) Continuation of application No. 15/418,764, filed on Jan. 29, 2017, now Pat. No. 10,624,785.
(Continued)

(51) Int. Cl.
*A61F 9/007* (2006.01)
*A61B 17/32* (2006.01)
(Continued)

(52) U.S. Cl.
CPC ...... *A61F 9/00754* (2013.01); *A61B 17/3203* (2013.01); *A61B 17/320016* (2013.01);
(Continued)

(58) Field of Classification Search
CPC .......... A61B 17/221; A61B 17/320016; A61B 17/32002; A61B 17/3203;
(Continued)

(56) References Cited

U.S. PATENT DOCUMENTS 1,833,687 A    11/1931  Neivert
1,891,054 A    12/1932  Pitman
(Continued)

FOREIGN PATENT DOCUMENTS

CN           2192307 Y      3/1995
CN         101495063 A      7/2009
(Continued)

OTHER PUBLICATIONS

U.S. Appl. No. 15/970,439, filed May 3, 2018, US 2018-0318132.
(Continued)

*Primary Examiner* — Benjamin J Klein
(74) *Attorney, Agent, or Firm* — Mintz Levin Cohn Ferris Glovsky and Popeo, P.C.

(57) ABSTRACT

A hand-held aspiration device is provided which has a relatively small suction volume along a suction path to improve responsiveness of the aspiration device when the device is activated. The device may be manually powered and may be provided without electronic controls. The device has a suction path which may be purged into a disposal enclosure to reduce the volume of material under the influence of the suction pressure during the procedure. The suction source may also be part of the hand-held unit to further reduce the suction path and suction volume.

11 Claims, 19 Drawing Sheets

Related U.S. Application Data

(60) Provisional application No. 62/289,197, filed on Jan. 30, 2016.

(51) Int. Cl.

| | | |
|---|---|---|
| *A61B 17/3203* | (2006.01) | |
| *A61F 9/013* | (2006.01) | |
| *A61B 17/3205* | (2006.01) | |
| *A61B 17/221* | (2006.01) | |
| *A61B 17/3207* | (2006.01) | |
| *A61B 17/00* | (2006.01) | |
| *A61F 9/00* | (2006.01) | |
| *A61F 9/008* | (2006.01) | |

(52) U.S. Cl.
CPC ...... *A61F 9/00736* (2013.01); *A61F 9/00781* (2013.01); *A61F 9/013* (2013.01); *A61B 17/221* (2013.01); *A61B 17/32002* (2013.01); *A61B 17/32056* (2013.01); *A61B 17/320725* (2013.01); *A61B 2017/00867* (2013.01); *A61B 2017/2212* (2013.01); *A61B 2017/320052* (2013.01); *A61B 2217/005* (2013.01); *A61B 2217/007* (2013.01); *A61F 9/008* (2013.01); *A61F 9/0008* (2013.01); *A61F 9/00745* (2013.01)

(58) Field of Classification Search
CPC ...... A61B 17/32056; A61B 17/320725; A61B 2017/00867; A61B 2017/2212; A61B 2217/005; A61B 2217/007; A61F 9/0008; A61F 9/00736; A61F 9/00745; A61F 9/00754; A61F 9/00781; A61F 9/008; A61F 9/013
See application file for complete search history.

(56) References Cited

U.S. PATENT DOCUMENTS

| | | |
|---|---|---|
| 2,947,470 A | 8/1960 | Ruben et al. |
| 3,589,363 A | 6/1971 | Banko et al. |
| 3,882,872 A | 5/1975 | Douvas et al. |
| 3,903,892 A | 9/1975 | Komiya |
| 3,908,661 A | 9/1975 | Kramer |
| 3,957,052 A | 5/1976 | Topham |
| 3,973,568 A | 8/1976 | Iglesias |
| 4,367,744 A | 1/1983 | Sole |
| 4,368,734 A | 1/1983 | Banko |
| 4,538,611 A | 9/1985 | Kelman |
| 4,643,187 A | 2/1987 | Okada |
| 4,693,245 A | 9/1987 | Pao |
| 4,705,500 A | 11/1987 | Reimels et al. |
| 4,732,150 A * | 3/1988 | Keener Jr. ........ A61B 17/32056 606/107 |
| 4,764,165 A | 8/1988 | Reimels et al. |
| 4,766,897 A | 8/1988 | Smirmaul |
| 4,791,924 A | 12/1988 | Kelman |
| 4,854,825 A | 8/1989 | Bez et al. |
| 4,869,716 A * | 9/1989 | Smirmaul ........... A61F 9/00736 606/107 |
| 4,888,015 A | 12/1989 | Domino |
| 4,891,044 A | 1/1990 | Mitchell |
| 4,908,015 A | 3/1990 | Anis |
| 4,950,272 A | 8/1990 | Smirmaul |
| 4,955,887 A | 9/1990 | Zirm |
| 4,960,418 A | 10/1990 | Tennant |
| 5,123,906 A | 6/1992 | Kelman |
| 5,146,921 A | 9/1992 | Terwilliger et al. |
| 5,147,369 A | 9/1992 | Wagner |
| 5,156,607 A | 10/1992 | Kansas |
| 5,171,314 A | 12/1992 | Dulebohn |
| 5,201,741 A | 4/1993 | Dulebohn |
| 5,222,959 A | 6/1993 | Anis |
| 5,222,960 A | 6/1993 | Poley |
| 5,242,449 A | 9/1993 | Zaleski |
| 5,275,607 A | 1/1994 | Lo et al. |
| 5,279,547 A | 1/1994 | Costin |
| 5,437,678 A | 8/1995 | Sorensen |
| 5,651,783 A | 7/1997 | Reynard |
| 5,676,649 A | 10/1997 | Boukhny et al. |
| 5,693,062 A | 12/1997 | Stegmann et al. |
| 5,728,117 A | 3/1998 | Lash |
| 5,788,679 A | 8/1998 | Gravlee, Jr. |
| 5,800,533 A | 9/1998 | Eggleston et al. |
| 5,807,401 A | 9/1998 | Grieshaber et al. |
| 5,843,071 A | 12/1998 | Bath |
| 5,891,153 A | 4/1999 | Peterson |
| 5,911,699 A | 6/1999 | Anis et al. |
| 5,938,677 A | 8/1999 | Boukhny et al. |
| 6,013,049 A | 1/2000 | Rockley et al. |
| 6,059,765 A | 5/2000 | Cole et al. |
| 6,074,396 A | 6/2000 | Geuder |
| 6,117,149 A | 9/2000 | Sorensen et al. |
| 6,120,496 A | 9/2000 | Whayne et al. |
| 6,132,436 A | 10/2000 | Portney |
| 6,165,190 A | 12/2000 | Nguyen |
| 6,183,433 B1 | 2/2001 | Bays |
| 6,241,700 B1 | 6/2001 | Leukanech |
| 6,254,587 B1 | 7/2001 | Christ et al. |
| 6,299,591 B1 | 10/2001 | Banko |
| 6,319,222 B1 | 11/2001 | Andrew et al. |
| 6,322,557 B1 | 11/2001 | Nikolaevich et al. |
| 6,328,747 B1 | 12/2001 | Nun |
| 6,379,370 B1 | 4/2002 | Feinsod |
| 6,398,754 B1 | 6/2002 | Sutton et al. |
| 6,428,508 B1 | 8/2002 | Ross |
| 6,506,176 B1 | 1/2003 | Mittelstein et al. |
| 6,520,929 B2 | 2/2003 | Zaleski |
| 6,520,955 B2 | 2/2003 | Reynard |
| 6,527,766 B1 | 3/2003 | Bair |
| 6,544,254 B1 | 4/2003 | Bath |
| 6,551,326 B1 | 4/2003 | Van Heugten et al. |
| 6,554,843 B1 | 4/2003 | Ou |
| 6,589,201 B1 | 7/2003 | Sussman et al. |
| 6,592,541 B1 | 7/2003 | Kurwa |
| 6,605,054 B2 | 8/2003 | Rockley |
| 6,623,477 B1 | 9/2003 | Elbrecht et al. |
| 6,743,228 B2 | 6/2004 | Lee et al. |
| 6,852,092 B2 | 2/2005 | Kadziauskas et al. |
| 6,860,868 B1 | 3/2005 | Sussman et al. |
| 6,939,317 B2 | 9/2005 | Zacharias |
| 6,939,341 B2 | 9/2005 | Vijfvinkel |
| 7,041,078 B1 | 5/2006 | Peyman |
| 7,083,589 B2 | 8/2006 | Banko et al. |
| 7,141,047 B2 | 11/2006 | John |
| 7,172,601 B2 | 2/2007 | Ben-Nun |
| 7,182,759 B2 | 2/2007 | Kadziauskas et al. |
| 7,204,820 B2 | 4/2007 | Akahoshi |
| 7,285,107 B1 | 10/2007 | Charles |
| 7,303,566 B2 | 12/2007 | Kishimoto et al. |
| 7,544,178 B2 | 6/2009 | Kadziauskas et al. |
| 7,588,553 B2 | 9/2009 | Dewey |
| 7,632,294 B2 | 12/2009 | Milbodker et al. |
| 7,845,235 B2 | 12/2010 | Sandu et al. |
| 7,846,126 B2 | 12/2010 | Steen et al. |
| 7,857,794 B2 | 12/2010 | Dimalanta et al. |
| 7,867,163 B2 | 1/2011 | Chin et al. |
| 7,876,025 B2 | 1/2011 | Ma et al. |
| 7,967,775 B2 | 6/2011 | Hong |
| 8,070,711 B2 | 12/2011 | Bassinger et al. |
| 8,142,388 B2 | 3/2012 | Gomez |
| 8,157,797 B2 | 4/2012 | Boukhny et al. |
| 8,246,644 B2 | 8/2012 | Rockley et al. |
| 8,287,484 B2 | 10/2012 | Rockley |
| 8,308,735 B2 | 11/2012 | Dimalanta |
| 8,317,739 B2 | 11/2012 | Kuebler |
| 8,376,983 B2 | 2/2013 | Ross et al. |
| 8,423,126 B2 | 4/2013 | Mackool |
| 8,475,480 B2 | 7/2013 | Mackool |
| 8,545,462 B2 | 10/2013 | Ghannoum |
| 8,771,301 B2 | 7/2014 | Boukhny et al. |
| 8,784,361 B2 | 7/2014 | Lane |

(56) References Cited

U.S. PATENT DOCUMENTS

| | | |
|---|---|---|
| 8,801,653 B2 | 8/2014 | Maaskamp et al. |
| 8,814,854 B2 | 8/2014 | Jia et al. |
| 8,852,139 B2 | 10/2014 | King et al. |
| 8,876,745 B2 | 11/2014 | Escaf |
| 8,876,747 B2 | 11/2014 | Kadziauskas et al. |
| 8,939,927 B2 | 1/2015 | Sorensen et al. |
| 8,986,290 B2 | 3/2015 | Patton |
| 9,050,171 B2 | 6/2015 | Foster |
| 9,144,517 B2 | 9/2015 | Kuebler et al. |
| 9,259,597 B2 | 2/2016 | Romano et al. |
| 9,351,871 B2 | 5/2016 | Ghannoum et al. |
| 9,370,611 B2 | 6/2016 | Ross et al. |
| 9,381,033 B2 | 7/2016 | Guo |
| 9,387,122 B2 | 7/2016 | Mackool |
| 9,402,766 B2 | 8/2016 | Akahoshi et al. |
| 9,433,725 B2 | 9/2016 | Schaller et al. |
| 9,439,807 B2 | 9/2016 | Koplin |
| 9,445,943 B2 | 9/2016 | Wilson et al. |
| 9,486,359 B2 | 11/2016 | Hauger et al. |
| 9,498,377 B2 | 11/2016 | McCary et al. |
| 9,498,378 B2 | 11/2016 | McDonell |
| 9,504,604 B2 | 11/2016 | Alvarez |
| 9,561,129 B2 | 2/2017 | Ross et al. |
| 9,566,188 B2 | 2/2017 | Raney et al. |
| 9,592,156 B2 | 3/2017 | Huang |
| 9,629,747 B2 | 4/2017 | Clauson et al. |
| 9,693,896 B2 | 7/2017 | Sussman |
| 9,724,238 B2 | 8/2017 | Heitel |
| 9,731,065 B2 | 8/2017 | Bourne et al. |
| 9,775,743 B2 | 10/2017 | Clauson et al. |
| 9,827,142 B2 | 11/2017 | Sasazaki et al. |
| 9,839,738 B2 | 12/2017 | Beauvais et al. |
| 9,861,522 B2 | 1/2018 | Sorensen et al. |
| 9,867,635 B2 | 1/2018 | Alvarez et al. |
| 9,878,075 B2 | 1/2018 | Sussman et al. |
| 9,889,247 B2 | 2/2018 | Akahoshi |
| 9,913,752 B2 | 3/2018 | Hauger |
| 10,278,861 B2 | 5/2019 | Bourne |
| 10,292,862 B1 | 5/2019 | Mackool |
| 10,294,934 B2 | 5/2019 | Bourne et al. |
| 2002/0019594 A1 | 2/2002 | McClellan et al. |
| 2002/0052617 A1 | 5/2002 | Anis et al. |
| 2002/0099400 A1 | 7/2002 | Wolf et al. |
| 2002/0151835 A1 | 10/2002 | Ross |
| 2003/0004455 A1 | 1/2003 | Kadziauskas et al. |
| 2003/0055387 A1 | 3/2003 | Sutton et al. |
| 2003/0074008 A1 | 4/2003 | Ou |
| 2003/0109867 A1 | 6/2003 | Gluche et al. |
| 2004/0010284 A1 | 1/2004 | Maloof et al. |
| 2004/0049217 A1 | 3/2004 | Ross et al. |
| 2004/0082902 A1 | 4/2004 | Kadziauskas et al. |
| 2004/0092800 A1 | 5/2004 | MacKool |
| 2004/0092982 A1 | 5/2004 | Sheffer |
| 2004/0116950 A1 | 6/2004 | Eibschitz-Tsimhoni |
| 2004/0153093 A1 | 8/2004 | Donovan |
| 2004/0199159 A1 | 10/2004 | Lee et al. |
| 2004/0220564 A1 | 11/2004 | Ho et al. |
| 2004/0220604 A1 | 11/2004 | Fogarty et al. |
| 2004/0243142 A1 | 12/2004 | Siepser |
| 2005/0113741 A1 | 5/2005 | Huang et al. |
| 2005/0234441 A1 | 10/2005 | Bisch et al. |
| 2005/0234473 A1 | 10/2005 | Zacharias |
| 2006/0135974 A1 | 6/2006 | Perkins |
| 2006/0253056 A1 | 11/2006 | Kadziauskas et al. |
| 2007/0260173 A1 | 11/2007 | Boukhny et al. |
| 2008/0086148 A1 | 4/2008 | Baker et al. |
| 2008/0188792 A1 | 8/2008 | Barrett |
| 2008/0300531 A1 | 12/2008 | Gills, Jr. |
| 2009/0048607 A1 | 2/2009 | Rockley |
| 2009/0054904 A1 | 2/2009 | Holmen |
| 2009/0137993 A1 | 5/2009 | Kurtz |
| 2009/0149840 A1 | 6/2009 | Kurtz |
| 2009/0156985 A1 | 6/2009 | Hottmann et al. |
| 2009/0171242 A1 | 7/2009 | Hibner |
| 2009/0204135 A1 | 8/2009 | Cote |
| 2009/0216225 A1 | 8/2009 | Ben-Nun |
| 2010/0030134 A1 | 2/2010 | Fitzgerald et al. |
| 2010/0094278 A1 | 4/2010 | Jia et al. |
| 2010/0191178 A1 | 7/2010 | Ross et al. |
| 2010/0292631 A1 | 11/2010 | Holden |
| 2010/0312170 A1 | 12/2010 | Maaskamp et al. |
| 2010/0312232 A1 | 12/2010 | Jia et al. |
| 2010/0312252 A1 | 12/2010 | Jia et al. |
| 2010/0331911 A1 | 12/2010 | Kovalcheck et al. |
| 2011/0015562 A1 | 1/2011 | Akahoshi |
| 2011/0054384 A1 | 3/2011 | Brown |
| 2011/0112466 A1 | 5/2011 | Dimalanta |
| 2011/0137231 A1 | 6/2011 | Sorensen et al. |
| 2011/0144638 A1 | 6/2011 | Heeren et al. |
| 2011/0282335 A1 | 11/2011 | Jia et al. |
| 2011/0295192 A1 | 12/2011 | Geuder |
| 2012/0004595 A1 | 1/2012 | Dubois et al. |
| 2012/0022434 A1 | 1/2012 | Lue et al. |
| 2012/0041358 A1 | 2/2012 | Mann et al. |
| 2012/0072197 A1 | 3/2012 | Ovchinnikov |
| 2012/0080502 A1 | 4/2012 | Morgan et al. |
| 2012/0089080 A1 | 4/2012 | Ross et al. |
| 2012/0158030 A1 | 6/2012 | Underwood et al. |
| 2012/0172905 A1 | 7/2012 | Lee Shee et al. |
| 2012/0259320 A1 | 10/2012 | Loesel et al. |
| 2013/0018385 A1 | 1/2013 | Keene et al. |
| 2013/0023894 A1 | 1/2013 | Saleh |
| 2013/0231605 A1 | 9/2013 | Walter |
| 2013/0282020 A1 | 10/2013 | Hunter |
| 2014/0052113 A1 | 2/2014 | Kuehnert et al. |
| 2014/0074011 A1 | 3/2014 | Charles |
| 2014/0074013 A1 | 3/2014 | McCary et al. |
| 2014/0081151 A1 | 3/2014 | Saimovici |
| 2014/0081266 A1 | 3/2014 | Dubois et al. |
| 2014/0114335 A1 | 4/2014 | Banko |
| 2014/0163455 A1 | 6/2014 | Wilson et al. |
| 2014/0180396 A1 | 6/2014 | Pike et al. |
| 2014/0194860 A1 | 7/2014 | Dick et al. |
| 2014/0236163 A1 | 8/2014 | Olson et al. |
| 2014/0257258 A1 | 9/2014 | Kurtz |
| 2014/0271251 A1 | 9/2014 | Bourne et al. |
| 2014/0309649 A1 | 10/2014 | Alvarez et al. |
| 2014/0358155 A1 | 12/2014 | DeBoer et al. |
| 2014/0364885 A1 | 12/2014 | Wells et al. |
| 2014/0378988 A1 | 12/2014 | Raybin et al. |
| 2015/0005578 A1 | 1/2015 | Jorgensen et al. |
| 2015/0005753 A1 | 1/2015 | Walter |
| 2015/0025450 A1 | 1/2015 | King et al. |
| 2015/0038894 A1 | 2/2015 | Urich et al. |
| 2015/0045806 A1 | 2/2015 | Urich et al. |
| 2015/0105791 A1 | 4/2015 | Truckai |
| 2015/0141801 A1 | 5/2015 | Jean et al. |
| 2015/0196426 A1 | 7/2015 | Kuebler et al. |
| 2015/0202081 A1 | 7/2015 | Eichler |
| 2015/0216728 A1 | 8/2015 | Keller |
| 2015/0257927 A1 | 9/2015 | Olson |
| 2015/0297407 A1 | 10/2015 | Saimovici |
| 2015/0305934 A1 | 10/2015 | Joo et al. |
| 2015/0306286 A1 | 10/2015 | Ross et al. |
| 2015/0328047 A1 | 11/2015 | Falck, Jr. |
| 2015/0335393 A1 | 11/2015 | Ciulla et al. |
| 2015/0359672 A1 | 12/2015 | Van Valen et al. |
| 2016/0022489 A1* | 1/2016 | Hartstra .......... A61F 9/00736 606/166 |
| 2016/0030241 A1 | 2/2016 | Siepser |
| 2016/0058614 A1 | 3/2016 | Ross et al. |
| 2016/0067091 A1 | 3/2016 | Wells et al. |
| 2016/0074220 A1 | 3/2016 | Ianchulev et al. |
| 2016/0089268 A1 | 3/2016 | Chon et al. |
| 2016/0095749 A1 | 4/2016 | Raney et al. |
| 2016/0095750 A1 | 4/2016 | Raney et al. |
| 2016/0106580 A1 | 4/2016 | Banko |
| 2016/0106893 A1 | 4/2016 | Zacharias |
| 2016/0128869 A1 | 5/2016 | Zacharias |
| 2016/0143780 A1 | 5/2016 | Gunn |
| 2016/0166432 A1 | 6/2016 | Kahook et al. |
| 2016/0175578 A1 | 6/2016 | Roholt |
| 2016/0346121 A1* | 12/2016 | Ianchulev .......... A61F 9/00763 |
| 2017/0007451 A1 | 1/2017 | Depenbusch |

(56) References Cited

U.S. PATENT DOCUMENTS

| | | |
|---|---|---|
| 2017/0007452 A1 | 1/2017 | Depenbusch |
| 2017/0020728 A1 | 1/2017 | McDonell |
| 2017/0027750 A1 | 2/2017 | Wiley |
| 2017/0087013 A1 | 3/2017 | Prats et al. |
| 2017/0143341 A1 | 5/2017 | Belson et al. |
| 2017/0151091 A1 | 6/2017 | Bourne et al. |
| 2017/0151378 A1 | 6/2017 | Raney et al. |
| 2017/0231647 A1 | 8/2017 | Saunders et al. |
| 2017/0312125 A1 | 11/2017 | Clauson et al. |
| 2017/0333252 A1 | 11/2017 | Biancalana et al. |
| 2017/0360607 A1 | 12/2017 | Price et al. |
| 2017/0367885 A1 | 12/2017 | Bourne |
| 2018/0028360 A1 | 2/2018 | Kozawa |
| 2018/0036171 A1 | 2/2018 | Clauson et al. |
| 2018/0049920 A1 | 2/2018 | Charles |
| 2018/0058438 A1 | 3/2018 | Ochoa |
| 2018/0064578 A1 | 3/2018 | Clauson et al. |
| 2018/0132998 A1 | 5/2018 | Page |
| 2018/0318132 A1 | 11/2018 | Clauson et al. |
| 2018/0318133 A1 | 11/2018 | Clauson et al. |
| 2019/0015252 A1 | 1/2019 | Lake et al. |
| 2019/0041665 A1 | 2/2019 | Widman et al. |
| 2019/0269557 A1 | 9/2019 | Clauson et al. |
| 2019/0282402 A1 | 9/2019 | Clauson et al. |
| 2020/0060875 A1 | 2/2020 | Clauson et al. |

FOREIGN PATENT DOCUMENTS

| | | |
|---|---|---|
| CN | 102271633 A | 12/2011 |
| CN | 103025281 A | 4/2013 |
| CN | 104736076 A | 6/2015 |
| EP | 0 994 281 A2 | 4/2000 |
| EP | 0870486 B1 | 11/2005 |
| EP | 1832259 B1 | 6/2009 |
| EP | 1556099 B1 | 7/2013 |
| EP | 1735030 B1 | 8/2016 |
| FR | 2655836 A1 | 6/1991 |
| GB | 1304324 A | 1/1973 |
| GB | 2018601 A | 10/1979 |
| GB | 2532596 B | 5/2017 |
| JP | 3069723 U | 6/2000 |
| RU | 2068251 C1 | 10/1996 |
| RU | 2143253 C1 | 12/1999 |
| RU | 31105 U1 | 7/2003 |
| RU | 2014124946 A | 12/2015 |
| WO | WO-99/59510 A1 | 11/1999 |
| WO | WO-2006/068650 A1 | 6/2006 |
| WO | WO-2007/011302 A1 | 1/2007 |
| WO | WO-2012/048348 A1 | 4/2012 |
| WO | WO-2013/039742 A2 | 3/2013 |
| WO | WO-2015/161149 A | 10/2015 |
| WO | WO-2016/036406 A1 | 3/2016 |
| WO | WO-2017/143272 A2 | 8/2017 |
| WO | WO-2017/161062 A2 | 9/2017 |
| WO | WO-2018/081295 A1 | 5/2018 |

OTHER PUBLICATIONS

U.S. Appl. No. 16/221,239, filed Dec. 14, 2018, US 2019-0183681.
U.S. Appl. No. 16/257,533, filed Jan. 25, 2019, US 2019-0151149.
U.S. Appl. No. 16/345,182, filed Apr. 25, 2019, US 2019-0282402.
U.S. Appl. No. 16/778,775, filed Jan. 31, 2020, US 2020-0289319.
PCT/US2020/16155, Jan. 31, 2020, WO 2020/160434.
PCT/US/2020/33141, May 15, 2020, WO 2020/236593.
PCT/US/2020/33142, May 15, 2020, WO 2020/247165.
"General Catalog for Inami Surgical Instrument." Inami & Co., Ltd. (1998). 2 pages. [English language translation].
"General Catalog for Inami Surgical Instrument." Inami & Co., Ltd. (1998). 2 pages. [Japanese language].
"Phaco-Section by Wire Snare—A New Technique of Non-Phaco Stitchless Surgery for Suprahard Cataracts." Basak, Samar K. (Jan. 30, 2013 published). URL: https://www.youtube.com/watch?v=CP8jrVb8qrg Retrieved from YouTube.com. May 28, 2019 1 page.
Bhattacharya, Debasish. (2009). "Nuclear management in manual small incision cataract surgery by snare technique." Indian J Ophthalmol. Jan.-Feb. 2009; 57 (1): 27-29.
Blumenthal, Michael et al. (1992). "Small-Incision Manual Extracapsular Cataract Extraction Using Selective Hydrodissection." Ophthalmic Surg., Oct. 1992; 23(10):699-701.
U.S. Appl. No. 16/404,252, filed May 6, 2019, US 2019-0254872.
U.S. Appl. No. 16/431,560, filed Jun. 4, 2019, US 2019-0365567.
U.S. Appl. No. 16/436,648, filed Jun. 10, 2019, US 2019-0321223.
U.S. Appl. No. 16/577,418, filed Sep. 20, 2019, US 2020-0022841.
U.S. Appl. No. 16/667,030, filed Oct. 29, 2019, US 2020-0060875.
U.S. Appl. No. 16/690,881, filed Nov. 21, 2019, US 2020-0197222.
U.S. Appl. No. 16/875,421, filed May 15, 2020, US 2020-0383833.
U.S. Appl. No. 16/875,426, filed May 15, 2020, US 2020-0360185.
U.S. Appl. No. 17/177,017, filed Feb. 16, 2021, US 2021-0161712.
U.S. Appl. No. 17/570,094, filed Jan. 6, 2022, US 2022-0233353.

* cited by examiner

DEVICES AND METHODS FOR OCULAR SURGERY

CROSS-REFERENCE TO PRIORITY DOCUMENT

This application is a continuation of co-pending U.S. patent application Ser. No. 15/418,764, filed Jan. 29, 2017, which claims the benefit of U.S. Provisional Application Ser. No. 62/289,197, filed Jan. 30, 2016. Priority of the filing dates are hereby claimed and the disclosures of the patent applications are hereby incorporated by reference in their entireties.

FIELD OF THE INVENTION

This invention generally relates to devices and methods for ocular surgery with one such procedure being removal of a lens from a human eye. More specifically the invention relates to capturing, fragmenting and extracting of lenticular or other tissue in ophthalmic surgery.

BACKGROUND

Certain types of conventional ophthalmic surgery require breaking up lenticular tissue and solid intraocular objects, such as the intraocular lens into pieces so that it can be extracted from the eye. For example, extraction of lenses for cataract surgery is one of the most common outpatient surgical fields with more than 3 million cases performed annually in the United States alone. During cataract surgery a commonly used method for lens extraction is phacoemulsification which uses ultrasonic energy to break up the lens and then aspirate the lens fragments through the instrument. Other methods of lens fragmentation and extraction may include the use of instruments such as hooks, knives, or laser to break up the lens into fragments and then extract through an incision in the cornea in an ab-interno approach. Intraocular, ab-interno fragmentation of the lenticular tissue is extremely important in cataract surgery in order to allow removal of cataracts from ocular incisions which are typically not exceeding 2.8-3 mm.

A disadvantage of some lens extraction techniques are unwanted complications from aspiration of the lens particularly with the use of phacoemulsification. Ultrasonic energy and high volume during phacoemulsification may create turbulent flow which may have a deleterious effect on the tissue within the eye such as the corneal endothelium.

A device or method which is capable of extracting lenticular tissue from the anterior chamber without damaging other ocular structures would be a significant advantage to existing tools and techniques.

Additionally, certain aspiration and inspiration configurations require large pieces of capital equipment as in the case of phacoemulsification or may require certain resources such as wall vacuum which may not be available in all surgical settings particularly in under developed areas.

A device or method which is capable of inspiration or aspiration with less capitally intensive equipment would be a significant benefit to many surgical settings. The aspiration device may be an independent tube or cannula or may be associated with another device such as a phacoemulsification unit ("phaco system"). Flow control and pressure control of phaco systems typically requires electronic control by a main console. A handpiece is used which has a suction line extending from the handpiece to the main console. The handpiece also typically has an inspiration line with inspiration driven by simple gravity feed or by flow controlled by the main console with a fluid bag/cartridge mounted to the console.

Another problem with phaco devices and other devices using a remote vacuum source is that the suction lines are long which means that they will often contain compressible material during the procedure, such as gas or compressible tissue, which affects the responsiveness of suction at the tip when suction is turned on and off. The problem of responsiveness is exacerbated by manually deformable/compliant hoses and lines which also respond to changes in pressure when starting and stopping suction which further delays initiation and termination of suction at the tip. Yet another problem with some systems is that the disposal enclosure is also exposed to vacuum pressure and, as such, the container and gas or other compressible material therein, also responds to changes in pressure and further contributing to the delay in initiation and termination of suction at the tip and contributing to the low responsiveness of some systems.

Still another problem with conventional methods and devices for aspirating material from the eye is that the suction opening can readily clog during the procedure. Suction must be stopped and, if necessary, the material removed independently with another instrument inside the eye. The necessity to stop the procedure and unclog the distal opening undesirably increases the procedure time and need for unnecessary manipulations of the instrument(s) in the eye.

A final problem with some devices is the cost and complexity of the systems. A lower cost alternative with the same or better performance would also be desirable alternative such as one not requiring a costly control console and electronic control system.

SUMMARY OF THE INVENTION

What is invented are novel methods and devices for intraocular fragmentation and removal of the lens and other tissues during intraocular surgery. In various embodiments an ocular surgical device is described which utilizes cutting strings, filaments, snares, baskets, bags, loops and other devices designed to engage and fragment the lenticular tissue and aid in its removal from the eye in a minimally invasive, ab-interno approach.

In other embodiments, novel devices and methods for inspiration and aspiration of fluids from the eye are described.

The aspiration device has improved responsiveness compared to some prior art devices using remote suction devices with long manually deformable/compliant suction lines. In one aspect of the present invention, a hand-held device is provided which may also be powered (manually) by the user and does not require electronic control. The device may further have a short suction path with a small suction volume. The device may include a hand-held suction source which, of course, eliminate the need for hoses from the handpiece to the console thereby greatly reducing the length of line and also the amount of material subject to the suction pressure which may compress or expand to reduce responsiveness.

In another aspect of the present invention, the device has a purging mechanism which purges the material from the suction path and into the disposal enclosure. The purging mechanism may be part of the suction device or may be a separate mechanism. In a specific aspect, the purging mechanism is a plunger which pushes the material in direction opposite the suction direction and into the disposal enclosure. A valve, which may be a one-way valve, permits the material to enter the disposal enclosure. The valve (or one-way valve) may also prevent the material from entering the disposal enclosure when material is suctioned along the suction path during use.

Purging the suction path during the procedure reduces the volume of material in the suction path compared to systems having long fluid lines to remote suction systems. Purging the suction line may occur in-between suction times and may be accomplished using a movable element which also creates the suction pressure. In a specific aspect, the movable element may be a spring-loaded plunger which is manually set.

In still another aspect, the suction device may include a movable element within the suction path. For example, the suction device may be the spring-loaded plunger which is manually actuated. Of course, any other suction device may be used including a pneumatic system with bladders and/or balloons, a deformable wall and roller system, or any other suitable system for creating suction pressure such as a venturi. The movable element of the suction device of the present invention may also be used to purge the suction path but the two functions may, of course, be separated and performed in different manners without departing from various and independent aspects of the present invention.

The present invention is also directed to reducing the likelihood of clogging by providing a restrictor which restricts material in the vicinity of the distal opening. The restrictor reduces the likelihood of clogging by restricting the material that can enter the distal opening. The restrictor may also be movable (longitudinally and/or rotationally) to clear material from in and around the opening and to gather material as well.

The present invention also includes a tissue manipulator and method of manipulating tissue. The tissue manipulator has a shaft having a lumen with a distal opening, A first loop has a first leg and a second leg with at least one of the first and second legs extending through the lumen. The first loop is movable from a collapsed position to an expanded position when the at least one of the first and second legs is advanced through the lumen and out the distal opening in the lumen. A second loop has a first leg and a second leg with at least one of the first and second legs extending through the lumen. The second loop being movable from a collapsed position to an expanded position when the at least one of the first and second legs is advanced through the lumen and out the distal opening in the lumen. The shaft may be sized for introduction of a distal end of the shaft into an eye.

The first loop may have an unbiased shape which bounds an area defined in an orientation that maximizes the area. The area has an effective diameter which is equal to the diameter of a circle having the same area. The first loop moves toward the unbiased shape when moving from the collapsed position to the expanded position. The effective diameter of the area of the first loop is 4.5 mm to 6.5 mm or can be 5.0 mm to 6.0 mm in the expanded position. The effective diameter of the unbiased shape of the second loop may be within 20% of an effective diameter of the expanded position of the first and/or second loops. In this manner, the first and/or second loops provide for a soft deployment and are flexible during use. Use of a superelastic material further enhances the flexibility of the first and second loops. To this end, the first and second loops may be formed of superelastic wire having a diameter of about 0.003 inch although any size may be used with any suitable cross-sectional shape.

The tissue manipulator may also include an intermediate element positioned between the first loop and the second loop. The intermediate element may be a third loop positioned between the first loop and the second loop. The intermediate element may include an interconnecting element extending between the first loop and the second loop. The interconnecting element may be integrally formed with the first loop and the second loop. Alternatively, the interconnecting element may be a flexible filament extending between the first loop and the second loop. The third loop may have the features of the first and second loops.

The first and second loops provide a controlled amount of exposed surface therebetween to control, and optionally cut, a controlled amount of the material. The exposed surface between the first loop and the second loop has an area of 15 mm(3) to 60 mm(3). Stated another way, the exposed surface between the first loop and the second loop is 3-10 times the effective diameter in the expanded position (or the unbiased position since they may be the same).

The exposed surface between the first loop and the second loop may have 2-8, 2-6, 2-4 or even just 2 independent cells when viewed in a radially inward direction relative to the orientation axis of the first and second loops. The exposed surface has an area which is at least 4 times larger than an surface area of the intermediate element when expanded between the first and second loops and viewed radially inward with respect to the loops. In this manner, the intermediate element does not take up an excessive amount of room as compared to some net-type devices.

The device may include a first support element extending from a distal end of the shaft when the first loop is expanded. The first support element may be an elongate element that extends to a free end. The first support element is positioned with the free end positioned within an area of the first loop when viewing the first loop along an orientation that maximizes the area of the first loop. A second support element which cooperates with the second loop in the same manner may also be provided. The first loop and/or second loop may have at least one interconnecting element extending from a first connection to the first loop to a second connection to the first loop or may be substantially free of any such interconnecting elements depending upon the desired use.

In yet another aspect of the present invention, the tissue manipulator has a concave element coupled to a first loop to form a basket. The concave element may have one end integrally formed with the first loop with the other end movable within the lumen independent of the first and second legs. Alternatively, both ends may be integrally formed with the loop. A second loop having another concave element may be provided to form another basket with the two baskets being movable relative to one another between a nested position and a position in which the two baskets oppose one another.

In use, the device is introduced into the eye with a distal end and distal opening of the shaft inside the eye. The first loop is expanded and the second loop is also expanded (simultaneously or independently). Material is positioned within the first and/or second loop and then the first and/or second loop is collapsed around the material to contain, manipulate or cut the material. Furthermore, a suction source may be coupled to the lumen to suction the material, fluid, and the cut material into the lumen or another lumen. The method may include all features of the device which are expressly incorporated here for all purposes.

In another aspect of the present invention, another device is provided which has a shaft having an elongate element that is bowed outwardly by biasing the elongate element with a load when deployed. The loop is movable from a collapsed position to an expanded position when a first shaft part (coupled to the first end of the elongate element) and a second shaft part (coupled to the second end of the elongate element) are moved relative to one another from a first position to a second position. Material is positioned in the loop and then cut by collapsing the loop. The loop may be expanded so that the loop advances between the capsular bag and a whole lens contained within the capsular bag.

The elongate element may have a first and a second flexible portion with an intermediate portion therebetween which is at least 1.5 more stiff in bending than the flexible portions. In another aspect, the first end may change in orientation relative to the proximal end of the shaft when deployed. The change in orientation may be provided by simply pinning or otherwise rotatably coupling the first end to the shaft so that the angle (orientation) changes by at least 120 degrees or 180 degrees+/−45 degrees when the first and second shaft parts move from the first position to the second position. The distal end of the shaft may also include a flexible portion which changes in orientation relative to the proximal portion of the shaft when the loop is expanded. The distal end may change in orientation by at least 30 degrees. The first end rotates so that the loop advances distally beyond a distal end of the shaft as the loop moves from the collapsed position to the expanded position. The second end may also be rotatably coupled to the shaft or may include the flexible portion. Use of and discussion of all aspects of the first flexible portion or the first end are equally applicable to the second end and are specifically incorporated herein. Furthermore, a mixture of first end and second end are also expressly incorporated such as a flexible first end and a rotatable second end.

These and other aspects and features will become evident from the following description of the preferred embodiments, drawings and claims.

DESCRIPTION OF THE PREFERRED EMBODIMENTS

During cataract surgery it is desirable to have a supply of balanced saline solution (BSS) delivered to the eye as well as a supply of suction to remove fluids and other materials. Certain ophthalmic surgical tips have the ability to inspirate and aspirate fluid through dual lumen designs. These devices must be connected to a supply of suction and pressurized BSS fluid.

Figure 1:
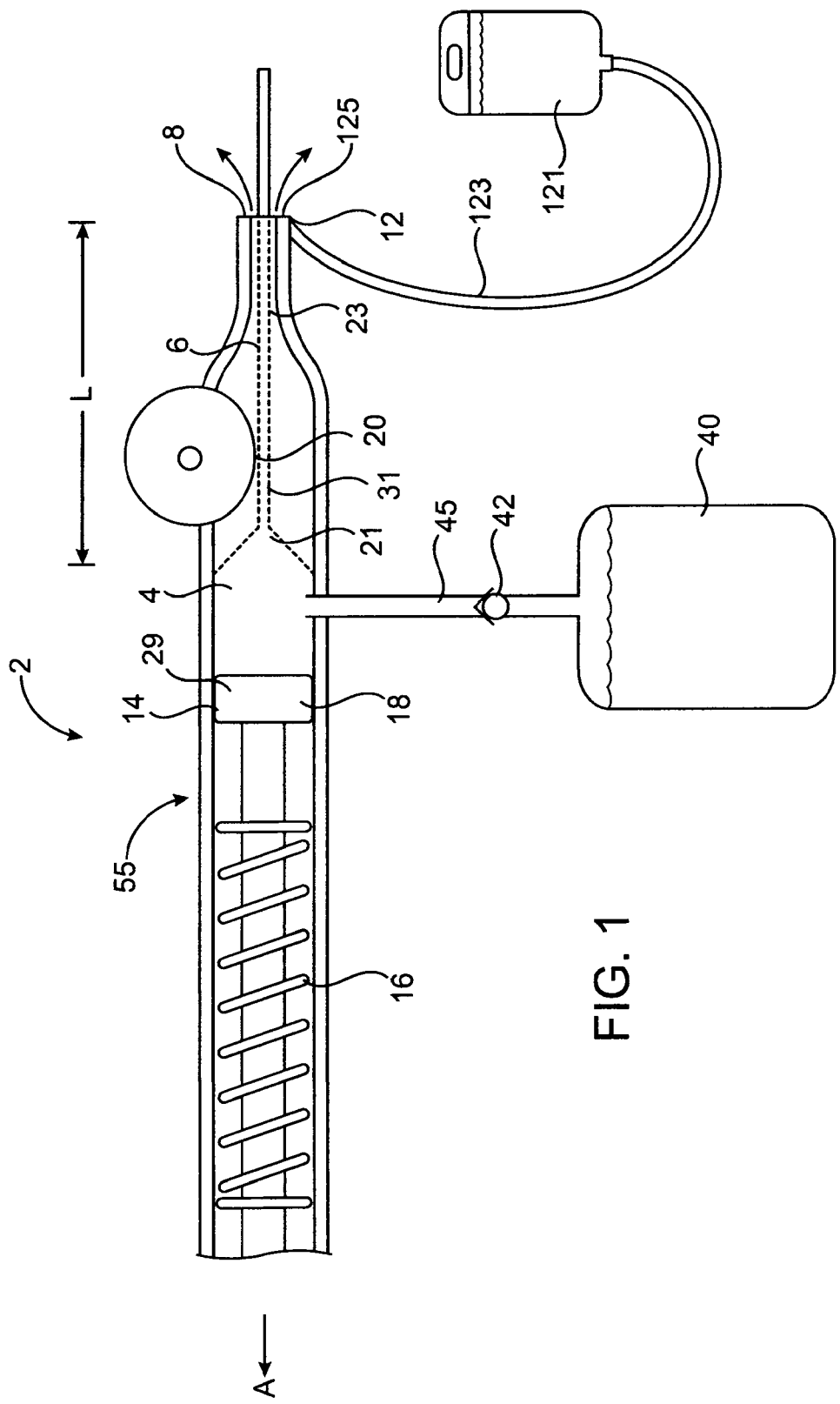
FIG. 1 shows a device for suctioning material.

In some embodiments, the invented device includes the ability to provide suction or BSS pressurized fluid through simple mechanisms, some of which may be manually powered or regulated. In FIG. 1 a separate plunger device is shown which may be depressed in order to create a vacuum which provides suction when connected to the hand piece. The hand piece may also be connected to a pressurized BSS source such as a hanging bag or any number of other pressurized sources such as spring loaded syringes and the like. Alternatively vacuum may be supplied by any number of other mechanisms such as a bellows mechanism, diaphragm pump, venturi pump, entrapment pump, positive displacement pump, regenerative pump, momentum transfer pump, sealed containers of vacuum that are released, micro pumps, or the like. When connected to a hand piece, suction is supplied to the tip to provide aspiration. In one embodiment, a compressible bulb such as a turkey baster may be used to provide suction. The user may depress the bulb with a finger and control the amount of suction by the release of the finger from the bulb. Other lever mechanisms may additionally create vacuum in a hand held instrument. In some embodiments, a nurse or assistant may create vacuum with a device that is connected to the hand held instrument. For example, a foot pedal may be used to create suction that is connect to the surgeons device. The hand piece may contain any number of waste containers that contain the withdrawn fluid and store it in the hand piece or off the hand piece. The various vacuum mechanisms may be powered in any number of ways such as a manual operation by the user or assistant. In this embodiment, the user may 'charge' the device with energy such as by depressing a spring loaded plunger before beginning the procedure and then controlling the amount of vacuum with a valve or other input mechanism. In some embodiments, the BSS pressurized supply may be coupled to the hand piece and may be 'charged' at the same time as the vacuum or separately. For example, the surgeon may depress one plunger that creates a spring force on the vacuum and the BSS fluid such that the surgeon may control the release of both with a single button or multiple buttons during the procedure. In other embodiments, the BSS may be in a hanging bag or other pressurized system and piped into the handpiece.

In some embodiments, the hand piece may include a flow control valve for additionally allowing the surgeon to select the rate or pressure of the fluids aspirated or inspirated. The surgeon may adjust the amount of flow desired by rotating a knob that compresses a tube a certain amount or opens a ball valve a certain amount or any number of other flow control mechanisms. The device may also include a button that can be depressed to regulate when the device is inspirating or aspirating. The amount the surgeon depresses the button may in itself control the variable flow. There may be a single button for controlling inspiration and aspiration or individual buttons for each. It should be understood that button simply means a control interface for the user and that any number of interfaces may be contemplated. Additionally the control interface may be on the hand held device or may be in another location. For example a foot pedal may be used to control the flow or a separate device held with a different hand may be used.

In some embodiments, the device may include a dual lumen design for inspiration and aspiration. In other embodiments, there may be more than 2 lumens or the lumens may be oriented concentrically.

In various other embodiments, device and methods for the removal or fragmentation of the lenticular tissue is described. Bags or meshes which are attached to snares or loops may be incorporated to grab lenticular tissue that is either whole or partially fragmented. The bags and meshes may be used to pull the tissue from the eye through a paracentesis. In some embodiments, a separate tool may be inserted into the bag or mesh after a fragment of the lens is captured and the separate tool may be used to break the tissue into smaller fragments. For example, a spinning cutter instrument may be inserted either with a different device or through a lumen of the bag device to cut the tissue into smaller pieces while it is within the bag or container so that may be withdrawn through the paracentesis.

In other embodiments, various baskets are used to capture the lens material and either pull it from the eye or further fragment the material into smaller pieces that may be aspirated. In each embodiment, the bags and meshes and baskets may be made of any number of materials. For example, nitinol material may be used and shaped into the proper orientation. Certain material such as nitinol may be elastically changed between multiple shapes and used to enter the eye through a small profile and expand within the eye to capture the lens material. Any number of shapes are contemplated such as coin purses, expanding balloons, curved bags, and the like. The devices may be comprised any plurality of materials such as stainless steel, nitinol, biocompatible plastics, and the like. Additionally, nitinol may be used in either its super elastic state or shape memory state or both in multiple components.

In some embodiments, cutter and augers and the like may be used to mechanically fragment the lens into multiple pieces. These devices may additionally include integrated suction for the aspiration of the lens material.

The aspects of the invention mentioned above are applicable to all suitable embodiments described herein. Thus, use of nitinol as described above is applicable to all suitable aspects concerning any cutting filament, element or device described herein. Similarly, any aspect of the aspiration device described above are equally applicable to all aspiration embodiments described herein. Finally, the features, aspects and methods of using each of the devices and methods is equally applicable to the other devices and methods described herein (including cutting) and all such features are expressly incorporated herein.

Referring to FIG. 1, a device 2 for removing material during procedures on the eye is shown. The device 2 has a suction path 4 which extends through a lumen 6 to an opening 8 in the lumen 6 at or near a distal end 12 of the lumen 6. The opening 8 is positioned in the eye for removal of material from the eye. A suction source 14 is coupled to the suction path 4 to draw material into the opening 8. The suction source 14 is a manually loaded spring 16 coupled to a plunger 18 but may be any other suitable source. The suction source 14 is also hand held providing for a short suction path 4 and the benefits of such a short path and small suction volume within the suction path 4.

The suction path 4 has a proximal suction volume 21 which may be substantially under the influence of suction pressure by the suction source 14 at all times so that the system is prepared or "primed," in a sense, to suction material. An actuator 20 is positioned near the opening 8 with the proximal volume of the suction path 4 less than 25 ml and already under suction pressure proximal to the actuator. The proximal volume is defined by the volume of the suction path 4 between the actuator and the suction source 14 (in this case the plunger 18). A distal volume 23 of the suction path 4 is also small since the actuator 20 is positioned relatively near the opening 8 and may be less than 2 ml. The actuator may be movable to a number of different positions and may be continuously variable to allow for the desired amount of suction by the user as described herein and specifically incorporated here. The term actuator 20 is used herein to refer to the element that acts on the suction path 4. A button 25 acts as an interface, however, the button or interface may be remote to the actuator 20. In this case, the button 25 acts directly on the actuator and may also have elastic properties itself.

The suction source 14 may have a movable element 29, such as the plunger 18, which is displaced in a direction shown by arrow A to draw the material into the opening and through the suction path 4. The movable element is displaced in an opposite direction to the direction A to move material into the suction path 4 into the disposal enclosure as explained in greater detail below in association with purging of the suction path 4.

The suction source 14 is hand-held in that the movable element is part of a hand held unit. The device also may have no electronic control and no electric powered parts and may even be powered by the user in that the spring 16 is manually loaded (extended). The movable element 29 is coupled to the spring 16 to manually load the movable element 29 with a spring load. The movable element 29 may be a piston, a plug, stopper, ball or a movable part of a wall such as a bladder or balloon. Once loaded, the movable element 29 continuously exerts suction pressure until the spring 16 is completely relaxed or otherwise restrained.

The actuator 20 also serves as a valve for the suction path 4 and may act on a deformable part 31 of the suction path 4. The opening 8 is exposed to suction pressure refers to the fact that suction pressure may be applied by exposing the opening to the suction pressure when activating the actuator. Alternatively, the opening 8 may be exposed to the suction pressure when activating the suction device itself. For example, even the spring-loaded mechanism of the device 2 may be coupled to a controller (not shown) so that suction pressure is applied and released and, when applied, exposes the opening 8 to suction pressure to draw material into the opening. Of course, responsiveness may be affected but other aspects of the present invention may, nevertheless, be practiced with on-demand suction. The actuator 20 may be continuously variable by simply depressing more or less to deform more or less of the deformable portion 31 between at least two different open positions. FIG. 1 shows a continuously variable actuator between the fully open and fully closed positions by simply varying the amount the deformable part 31 is deformed.

A disposal enclosure 40 is coupled to the suction path 4 to receive material from the suction path 4. A valve 42, such as a one-way valve, is positioned between the disposal enclosure 40 and the suction path 4. The valve 42 permits material to move to the disposal enclosure 40 and isolates the disposal enclosure 40 during suction operation. The valve 42 may be an actuated valve or a passive one-way valve which opens and closes automatically as necessary. The valve 42 isolates the disposal enclosure 40 so that the compressibility of the material does not affect the responsiveness of the system as described herein. The suction path 4 may increase in diameter at parts outside the eye similar to or the same as a syringe. Furthermore, the suction path 4 may take any shape without departing from the invention.

The disposal enclosure 40 is configured to be supported independently, for example, by the table a traditional hanger, or any other suitable structure. Furthermore, aspects of the present invention may be practiced with the disposal enclosure 40 hand-held or remotely located without departing from aspects of the invention. The disposal enclosure 40 has a disposal lumen 45 extending from the suction path 4 to the disposal enclosure. As mentioned above, the valve 42 (or one-way valve) isolates the disposal enclosure 40 from the suction pressure thereby preventing any pressure response by the disposal enclosure 40 during use. Of course, aspects of the present invention may be practiced without the valve 42.

The device 2 is hand-held to a large extent in that the suction path 4 is hand-held and the suction source 14 is hand-held as well. Within the meaning of the present invention, the suction source 14 does not include tubing or the like from the suction machine but defines the mechanical source that is creating the suction pressure. Although the present invention describes specific suction mechanisms and devices any other may be used. For example, a roller with tubing, a pneumatic system, a bladder or venturi may be used to create suction pressure without departing from aspects of the invention. The suction path 4 may also be more than half non-manually deformable or even at least 90% non-manually deformable. Most systems with remote suction devices include manually deformable tubes and hoses which may respond to pressure changes which further reduces responsiveness. The suction path 4 may be small to further improve responsiveness. To this end, the suction path 4 may have a length (longitudinal) L of less than 20 cm or a volume of less than 25 ml and even less than 15 ml.

As mentioned above, the present invention is particularly useful for removing material from the eye. As such, the lumen 6 may be appropriately sized. The suction path 4 includes a shaft 51 having the lumen 6. The lumen is sized for introduction into the eye and has a longitudinal axis with a cross-sectional area of the outer perimeter (or diameter) of the shaft 51 being no more than 0.8 mm(2) while the lumen has a cross-sectional area of at least 0.28 mm(2).

The plunger 18 is also operated to manually purge the suction path 4. Purging the suction path 4 reduces the material in the suction path 4 when suction is reinitiated. In this manner, the devices and methods of the present invention provide improvements in responsiveness compared to systems having long lines containing relatively large amounts of material between the handpiece and remote suction source 14.

A purging mechanism 55 may be the movable element 29 (plunger 18) or may be a separate element which moves the material from the suction path 4 to the disposal enclosure. In one aspect, the purging mechanism moves the material through the suction path 4 in an opposite direction to suction of material along the suction path 4 as shown by arrow A. The valve 42 permits flow from the suction path 4 to the disposal enclosure 40 when the movable element 29 is advanced. The purging mechanism 55 may also include an element separate from the movable element 29 which forms part of the suction device and may be completely independent of the suction source 14. As defined herein, the suction path 4 includes volumes occupied by movable elements 29. For example, the plunger 18 moves between fully retracted and fully advanced positions with the suction path 4 essentially changing in length and in volume. As used herein, the defined length and volume of the suction paths shall be defined with the minimum volume contained therein by the suction source 14. Thus, the length and volume is defined by the most advanced position of the plunger/movable element that minimizes the length and volume.

As described herein, "compressible" material such as a gas may also refer to the "expansibility" of the material in that suction pressure applied to entrained gas and material may permit the gas and material to expand slightly under the lower suction pressure (rather than compress). The compressibility (or expandability) of gasses and the effect on pressure responsiveness is typically deemed a problem of "compressibility" of gasses and is also so described herein and it is understood that this term also applies to the expandable nature of gasses and materials. With respect to the hoses and lines, the ability to resist compression by the suction pressure is a material property relevant to the responsiveness of such systems with manually deformable materials typically also responding mechanically to pressure variations.

Figure 2:
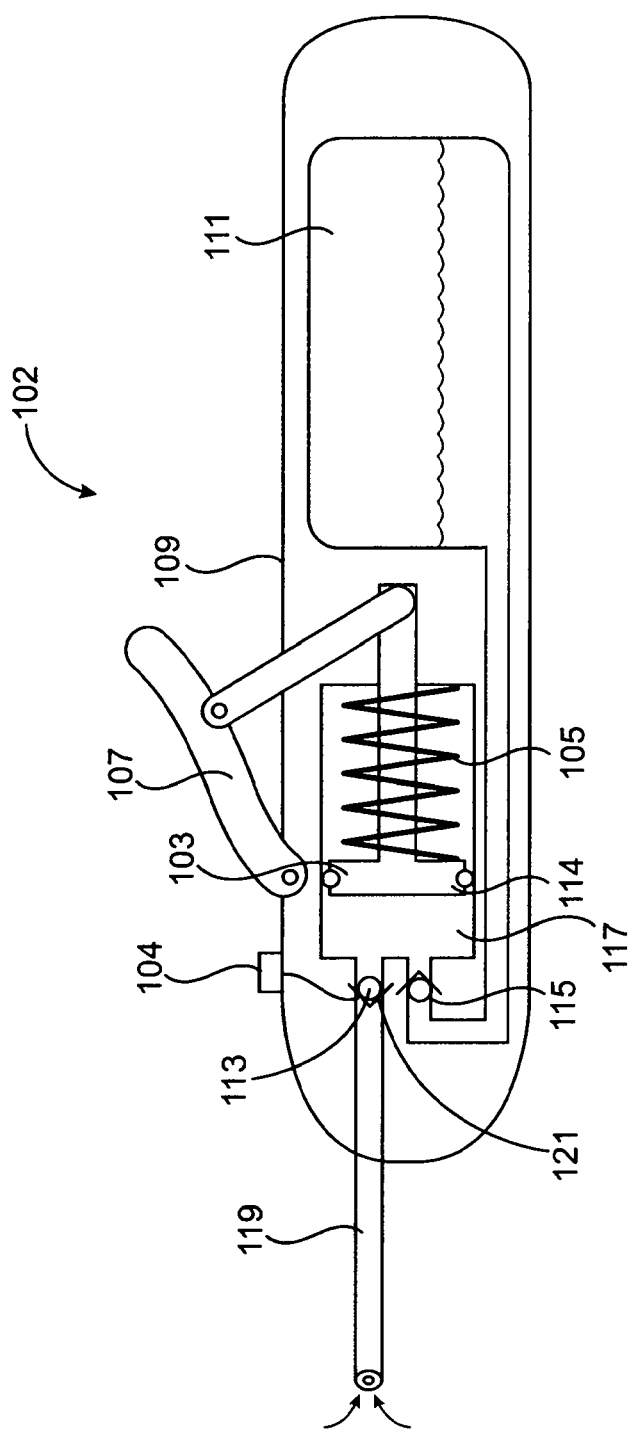
FIG. 2 shows another device for suctioning material.

Referring to FIG. 2, another suction device 102 is shown wherein the same or similar reference numbers refer to the same or similar structure. The suction source 114 is also a plunger 103 which is manually loaded with a spring 105. The spring 105 is loaded with a pivoting lever 107 attached to a housing 109. The disposal enclosure 111 is also mounted to and within the housing 109 and is hand-held with the device 102. Pressing the lever 107 advances the plunger 103 to purge the material in suction path 4 to the disposal enclosure 111. A first valve 113 and a second valve 115 (which may be one-way valves) permit suction through the lumen and purging of material into the disposal enclosure 111.

The lever 107 may be selectively locked and unlocked once advanced or the user may continue to apply pressure to the lever 107 to essentially stop suction. When suction is desired again, the lever 107 may be released with variable pressure to vary the amount of suction produced. Alternatively, the first valve 113 may include an interface 115, such as a button, which is actuated to open and close the suction path 104. The interface 114 may act as an actuator described herein and separates a proximal volume 117 from a distal volume 119 of the suction path 104. The first valve 113 may be formed over a deformable portion 121 of the suction path 104 along the valve 113 for use as described herein and all such uses of the deformable portion and actuator are expressly incorporated here. The second valve 115 (which may be a one-way valve) regulates flow to the disposal enclosure 111. A source of irrigation fluid 121 is also coupled to the shaft for irrigating the eye using a source of irrigation fluid 121. The source of irrigation fluid 121 may be a gravity fed bag or part of a fluid delivery system such as a phaco system. An irrigation lumen 123 has an opening 125 positioned in the eye for delivery the irrigation fluid.

Figure 3:
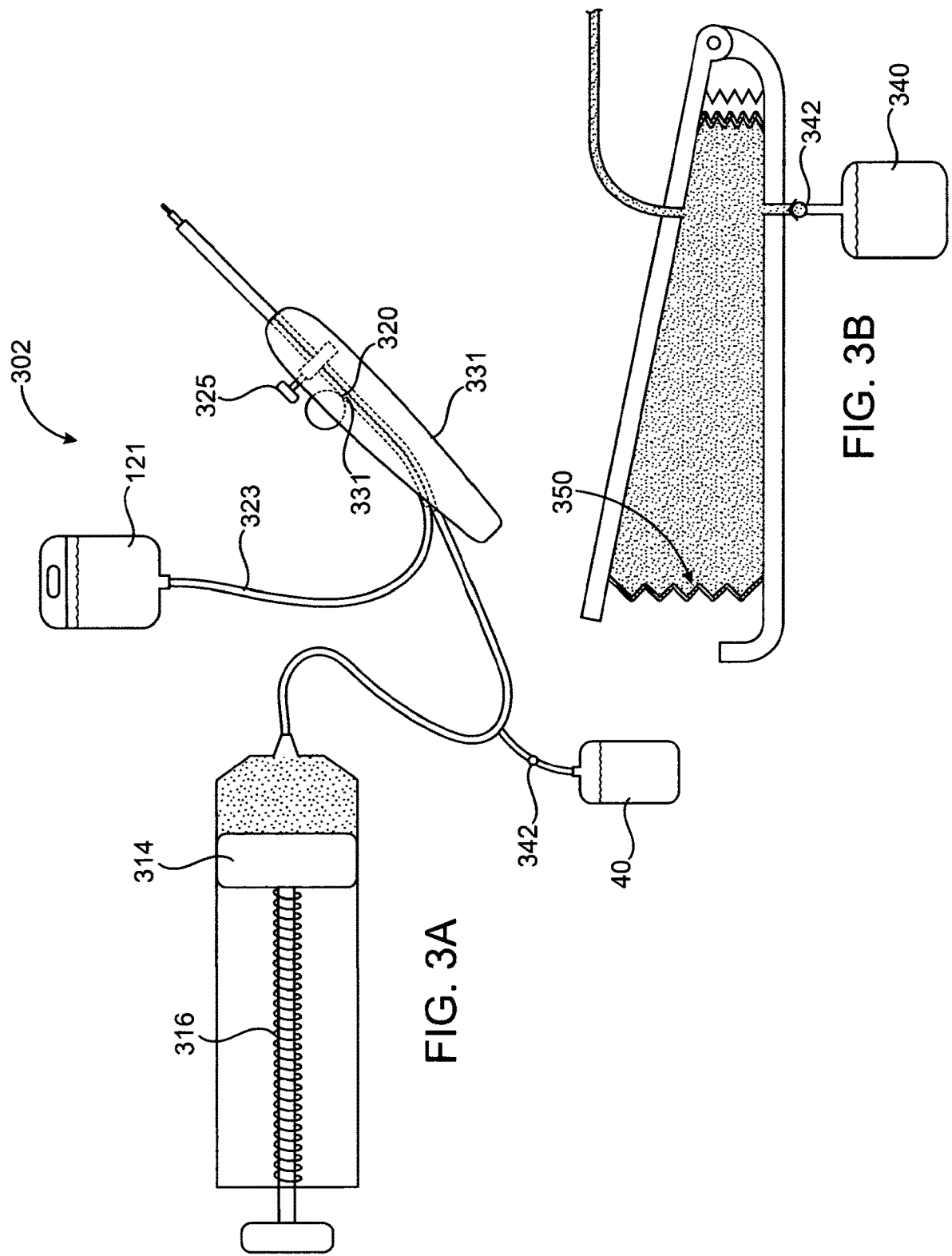
FIG. 3A shows still another device for suctioning material.
FIG. 3B shows an alternative suction source using a bellows.

Referring to FIG. 3A, another suction device 302 is shown wherein the same or similar reference numbers refer to the same or similar structure. The suction source 314 is also a plunger 318 or movable element 329 which is manually loaded with a spring 316, however, the suction source 314 is remote from the hand-held housing 331. The spring is loaded manually. An irrigation source 121, such as a bag of balanced saline solution, is coupled to an irrigation lumen 323. A valve 325 controls flow of the irrigation fluid. The actuator 320 is used in the same manner as the actuator 20 above and suction path 304 includes the deformable portion 331 and all aspects and methods of these elements are incorporated expressly here. Purging of the suction path 104 is also accomplished in the same manner with the material moving into the disposal enclosure when the movable element 329, such as the plunger 318, is advanced. A valve 342 may be are provided in the same manner as described above for controlling the flow into the disposal enclosure 40 and discussion of these aspects are also incorporated here.

Referring to FIG. 3B, the suction source 314 may also be a bellows 350 (rather than the plunger) which may be actuated by foot with a foot pedal. The bellows 350 are biased to an open position so that the bellows 350 provides suction after the foot pedal is depressed. Similar to other embodiments, when the bellows 350 is compressed by the user's foot the material within the bellows 350, which also constitutes part of suction path 304 as described herein, is moved to the disposal enclosure 340.

Figure 4:
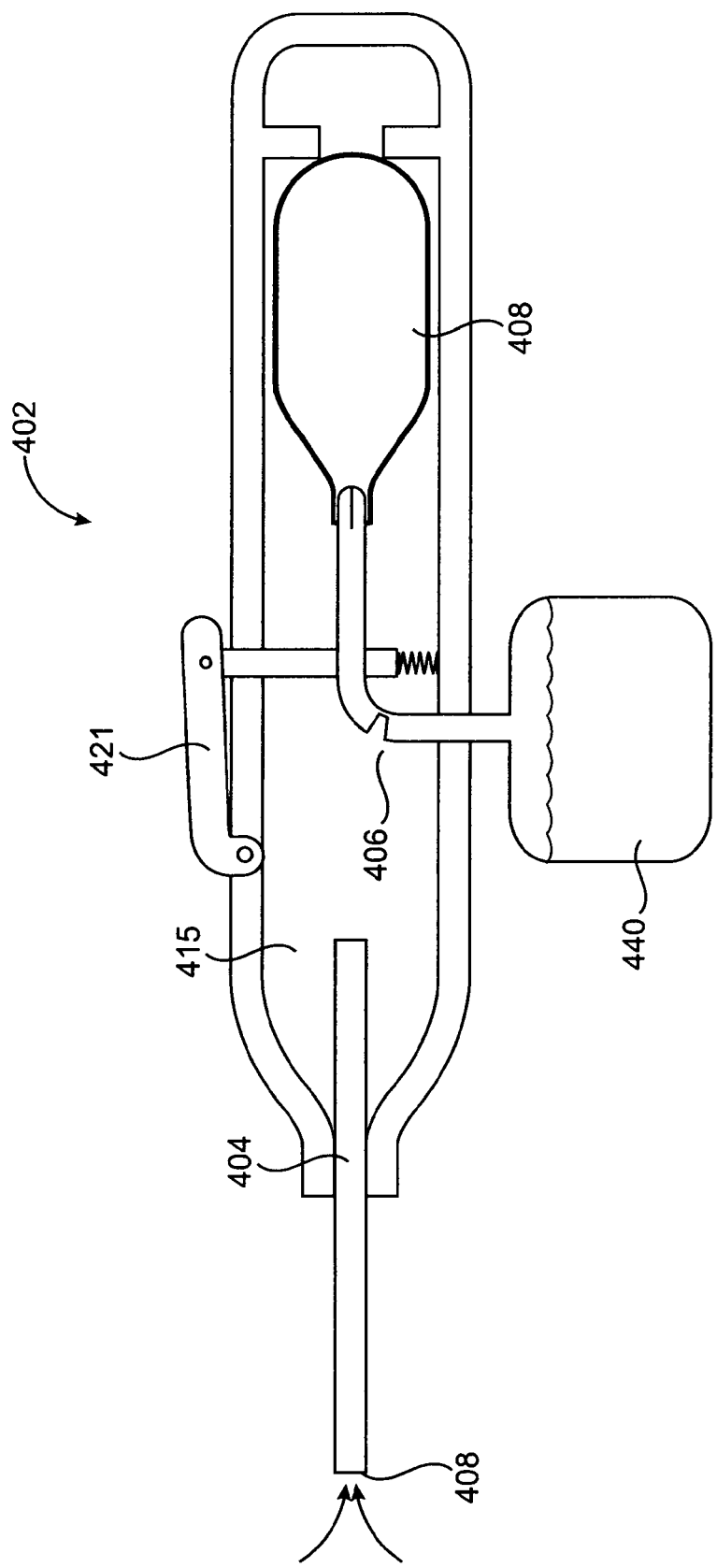
FIG. 4 shows yet another suction device using a venture.

Referring to FIG. 4, yet another suction device 402 is shown wherein the same or similar reference numbers refer to the same or similar structure. The device 402 has a venturi 406 coupled to a source of pressurized gas 408. The venturi 406 directs the pressurized gas toward the disposal enclosure 440 which also directs the material within suction path 404 also toward the disposal enclosure 440. The venturi 406 also acts as the suction source 414 producing suction pressure along the suction path 404. The suction path 404 includes a 415 chamber in communication with the venturi 406 so suction pressure is created in the chamber 415 by the venture 406. The venturi 406 is opened and closed with a pivoting lever 421.

Figure 5:
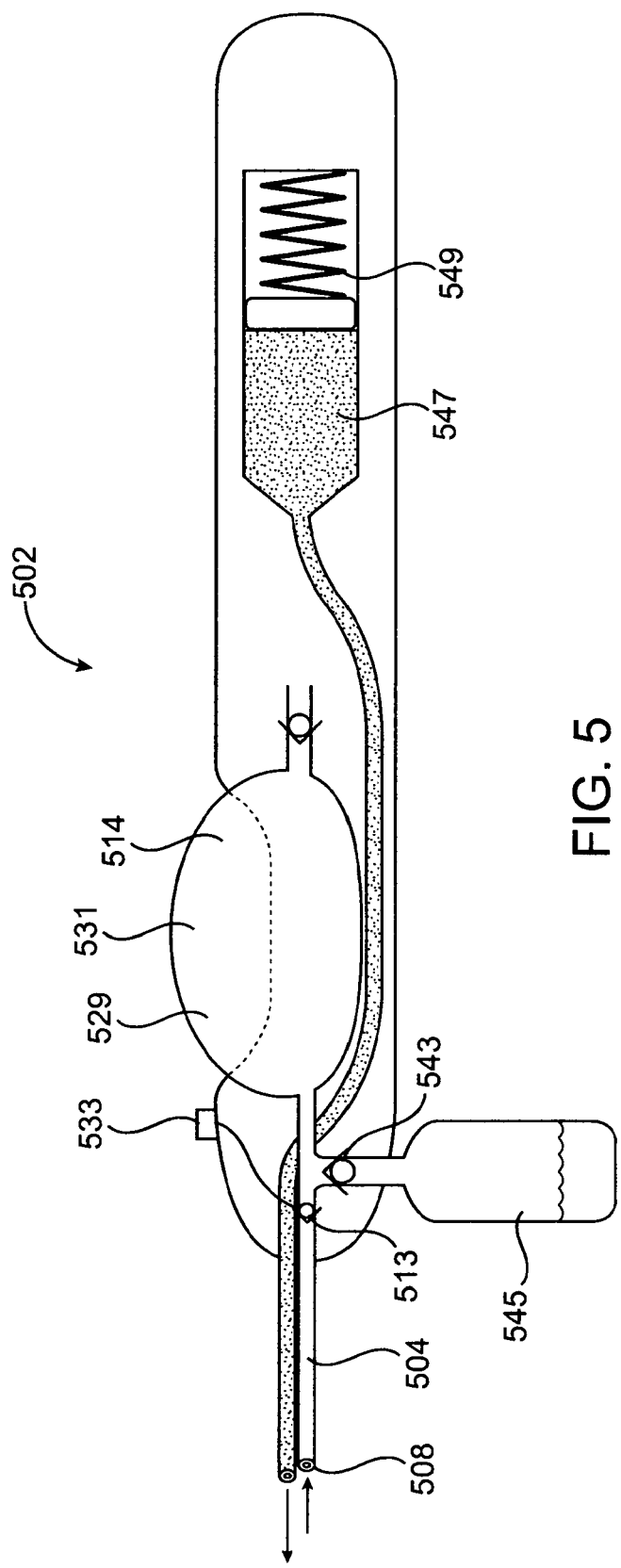
FIG. 5 shows still another suction device having a bladder as the suction source.

Referring to FIG. 5, another suction device 502 is shown wherein the same or similar reference numbers refer to the same or similar structure. The suction source 514 has a movable element 529 which a bladder 531 which is deformed manually by the user. Once compressed, compression is maintained on the bladder 531 to stop suction and reduced to produces suction. Stated another way, the bladder 531 is moved from an unbiased stated to a compressed state with the user releasing compression to begin suctioning material into the opening 508. Movement of the bladder 531 from the unbiased state to the compressed state may also move material from the suction path 504 (which includes the internal volume of the bladder) to the disposal enclosure. A first valve 513 may also include an interface, such as a button 533, so that the first valve 533 acts as the actuator described herein and separates a proximal volume 535 from a distal volume 537 of the suction path 504. The first valve 513 may be formed over a deformable portion 541 of the suction path 504 along the valve 513 as described herein. A second valve 543 (which may be a one-way valve) regulates flow to the disposal enclosure 545. An irrigation source 547 may also be provided with a spring loaded delivery 549 coupled to an actuator (not shown).

All aspects and methods of the suction devices described herein are applicable to the other suction devices and all such methods and aspects are expressly incorporated for each from the others. For example, the suction path length and volume as well as dimensions of the lumen and shaft are applicable to each of the other suitable embodiments described herein.

Figure 6A:
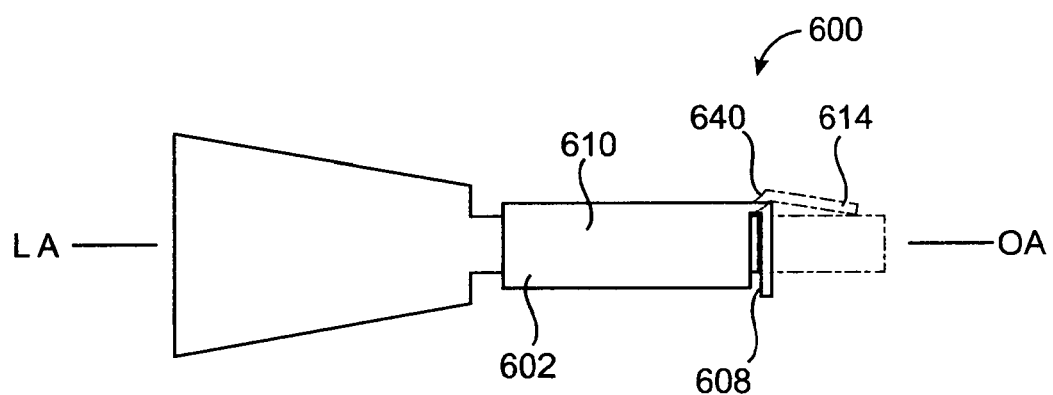
FIG. 6A shows a flow restrictor covering an opening in a shaft and in a stored position in the dotted-line position.
Figure 6B:
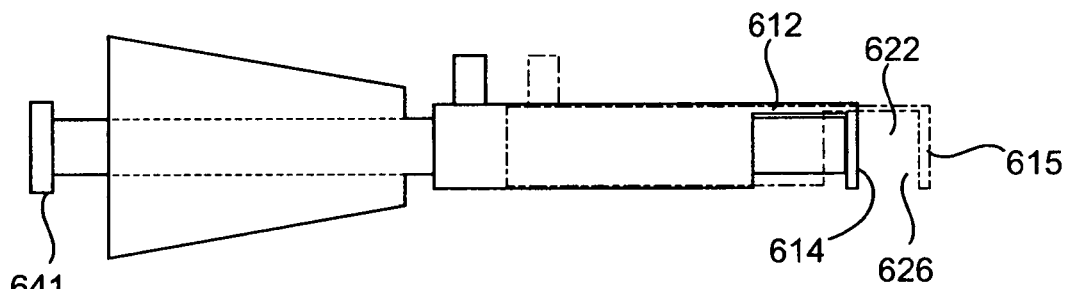
FIG. 6B shows the flow restrictor movable longitudinally relative to the shaft with the dotted line position showing a working position.
Figure 6C:
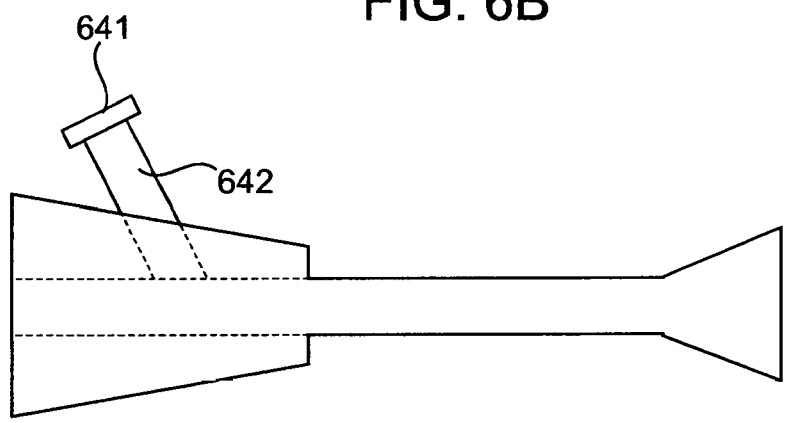
FIG. 6C shows show an alternative shaft having a y-arm.

Referring now to FIGS. 6A-6C, a suction tip 600 is shown for suctioning material from the eye. The suction tip 600 has a shaft 602 with a lumen 604 extending through the shaft 602. A distal opening 608 in the shaft 602 has an area which is defined by an opening axis OA which maximizes a size of the opening 608. The opening area may be circular, oval or any other suitable shape. The opening area defines an effective diameter defined as the diameter equivalent for a circle having the same area as the opening area.

Figure 7:
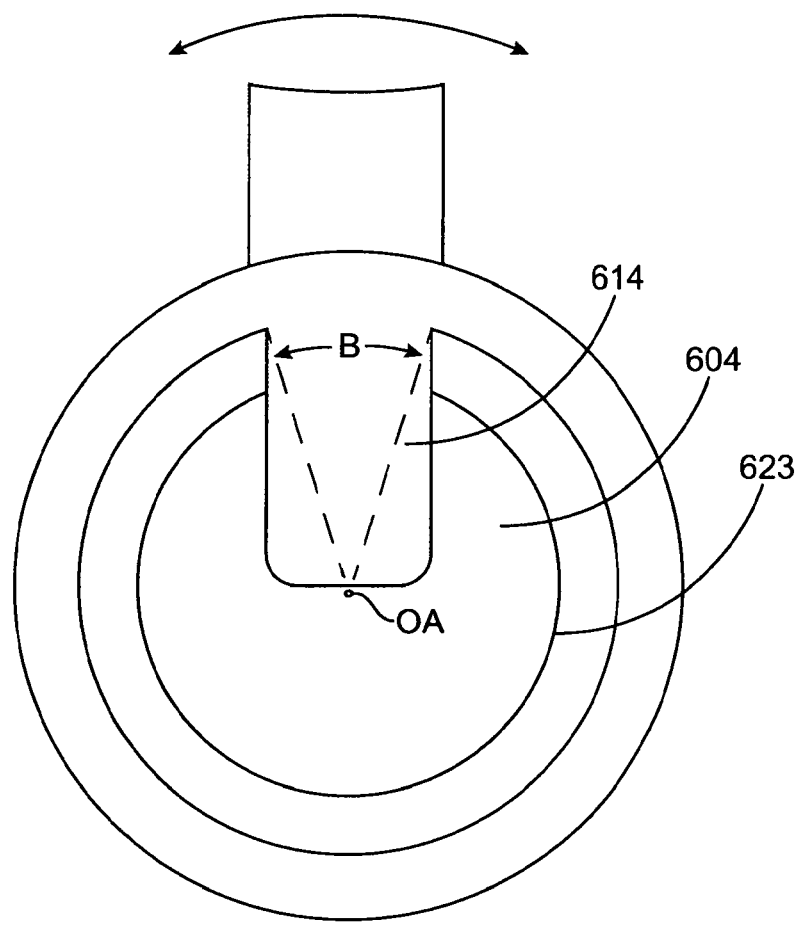
FIG. 7 shows an end view of the flow restrictor.

The suction tip also 600 has a restrictor 610 which extends over the distal opening 608 when viewed along the opening axis OA. The restrictor 610 has a support arm 612 extending from the shaft 602. The restrictor 610 may have a stop 614 attached to the support arm 612 with the stop 614 spaced apart from the distal opening and positioned over the distal opening when viewed along the opening axis as shown in FIG. 7. The restrictor 610 is spaced apart from the distal opening 0.80 to 1.10 times, or 0.85 to 1.00 times, the effective diameter measured along the opening axis and aligned with the distal opening when viewed along the opening axis. The restrictor 610 also may optionally extend a short distance from the distal end of the shaft so that it does not impede use. To this end, the restrictor 610 may have a distal end 615 that extends no more than 1.5 times the effective diameter from the distal opening measured along the opening axis. The restrictor has an area when viewed along the opening axis which may be 0.1 to 1.2 times the area of the distal opening when viewed along the opening axis. Thus, the restrictor may be somewhat small when less concerned with moving, gathering or clearing material from the opening.

The support arm 612 may have an angular extent B when viewed along the opening axis of no more than 90 degrees as shown in FIG. 7. The distal opening 604 may be free of obstruction apart from the support arm between the distal opening and a stop on the restrictor when viewed along the opening axis OA. The restrictor 610 forms a feed opening 622 leading to the distal opening 604 when the restrictor 610 is in the working position shown by the dotted-line position of FIG. 6B. The feed opening 622 defines a surface 626 extending between and defined by the restrictor 610 and a distal end of the shaft 623 around the opening 604. The surface 626 may be an elongate surface that, essentially, extends from one side of the support arm 612 to the other. In this manner, an average length of the surface is 2.5-3.5 times the effective diameter. The surface may have a width of 0.8 to 1.1 times the effective diameter.

The support arm 612 may be longitudinally and/or rotatably movable relative to the shaft to adjust a longitudinal or rotational position of the support arm as shown in the dotted-line and solid line positions. The support arm 612 is movable from a working position (as defined above) to a displaced position with the working position being a position used when suctioning material into the distal opening. The shaft has a longitudinal axis LA and the restrictor is formed with the support arm 612 rotating and/or longitudinally displaceable. The restrictor 610 may be formed so that the displaced position moves material toward the distal opening 608. The restrictor 610 may also be extended outwardly to help gather or otherwise organize material to be suctioned. The restrictor 610 may be movable to a position which is at least two effective diameters from the distal opening 608 measured along the opening axis.

The restrictor 610 may be mounted over the shaft, for example, in a concentric manner although an interlocking or independent lumens may be used without departing from the scope of the invention so long as the restrictor 610 is over the shaft and outside the lumen in some embodiments. The restrictor 610 is movable to a stored position in which the entire restrictor is positioned proximal to the distal opening and optionally completely outside the lumen as shown in the dotted-line position of FIG. 6A. Thus, the user may elect to use the suction device without restriction, for example, when the likelihood of clogging the opening is low. The restrictor 610 may be deformed when in the stored position and, to this end, the restrictor 610 has a living hinge 640 with the support arm 612 forming part, or all, of the living hinge 640 which is deformed in the stored position.

The stop 614 may be part of the support arm 612 in that the distal end of the support arm 612 simply forms the stop 614. Furthermore, the restrictor 610 may also simply be part of an extension of the shaft without departing from various aspects of the present invention. Finally, the restrictor 610 and methods associated with the restrictor 610 may be used with any of the other devices described herein including those associated with cutting and/or removing the lens. Furthermore, the devices may be used through the lumen of any of the devices described herein by simply providing a y-arm 642 and a suitable connector 641 which forms a seal around the cutting device. Thus, the lumen may be a substitute for any lumen described herein and the method of cutting the lens in combination and aspirating material and the device combination including any lens cutting device coupled with any aspirating device being specifically incorporated herein. For example, referring to FIGS. 6B and 6C, a seal is provided at the Y-arm 642 in the lumen and suction path through which any of the cutting devices described herein (or another cutting device) may be introduced. FIG. 6B shows the seal centrally located rather than on a Y-arm so the cutting device extends directly through the lumen with suction in the annular space between the cutting device and the shaft. Furthermore, an irrigation lumen, which may be concentric or separate, may be provided and the process of irrigating may be practiced with any method or combination method described herein and such methods are specifically incorporated here as shown in one or more embodiments and expressly incorporated into those which do not.

In use, the distal end of the shaft is positioned in the eye for any procedure on the eye including cataract surgery. During cataract surgery pieces of the cataract are removed using suction. The present invention may be used for this purpose as now described. Material is suctioned into the distal opening by applying suction which draws material into the distal opening. The restrictor 610 may help to reduce clogging of the distal opening compared to conventional suction devices which permit unrestricted flow toward the distal opening. As mentioned above, a problem with the conventional method is that material which is larger than the suction opening is free to approach and, thus, clog the opening. Suction must be stopped and, if necessary, the material removed independently by another instrument. The present invention is directed to reducing the likelihood of clogging by providing the restrictor. The present invention may be used with any device including a stand-alone aspiration device, a re-usable phacoemulsion tip, or a disposable aspect of any aspiration device.

Figure 8A:
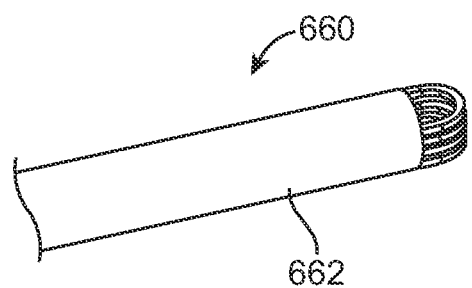
FIG. 8A shows a tissue manipulator in a collapsed position within a lumen of a shaft.

In another aspect of the present invention, a tissue manipulator 660 and method of manipulating tissue are described. The tissue manipulator 660 has a shaft 662 having a lumen 664 with a distal opening 668. A first loop 670 has a first leg 672 and a second leg 674 with at least one of the first and second legs 672, 674 extending through the lumen 664. The first loop 670 is movable from a collapsed position of FIG. 8A to an expanded position of FIG. 8B when the first and second legs are advanced through the lumen 664 and out the distal opening 668. A second loop 676 has a first leg 678 and a second leg 680 with the first and second legs 678, 680 extending through the lumen 664. The second loop 676 is also movable from a collapsed position to an expanded position when the first and second legs are advanced through the lumen and out the distal opening 668. The shaft 662 may be sized for introduction of a distal end of the shaft into an eye.

The first loop 670 may have an unbiased shape which bounds an area defined in an orientation OR that maximizes the area. The area has an effective diameter which is equal to the diameter of a circle having the same area. The first loop 670 moves toward the unbiased shape when moving from the collapsed position to the expanded position. The effective diameter of the area of the first loop is 4.5 mm to 6.5 mm or can be 5.0 mm to 6.0 mm. The effective diameter of the unbiased shape of the first and/or second loops may be within 20% of an effective diameter of the expanded position of the first and/or second loops, respectively. In this manner, the first and/or second loops provide for a soft deployment and are flexible during use. Use of a superelastic material further enhances the flexibility of the first and second loops. To this end, the first and second loops 670, 676 may be formed of superelastic wire having a diameter of about 0.003 inch although any size may be used with any suitable cross-sectional shape.

The first and second loops are each defined by the orientation OA which maximizes an area of the first loop and second loop when in the expanded position when viewed along each orientation. The orientation of the first and/or second loop may be within 45 degrees of perpendicular to the longitudinal axis LA at a distal end of the shaft. The first loop 670 is spaced apart from the second loop 676 to define a volume V therebetween when the first and second loops are in the expanded position with the volume therebetween being 48-84 mm(3).

Figure 8B:
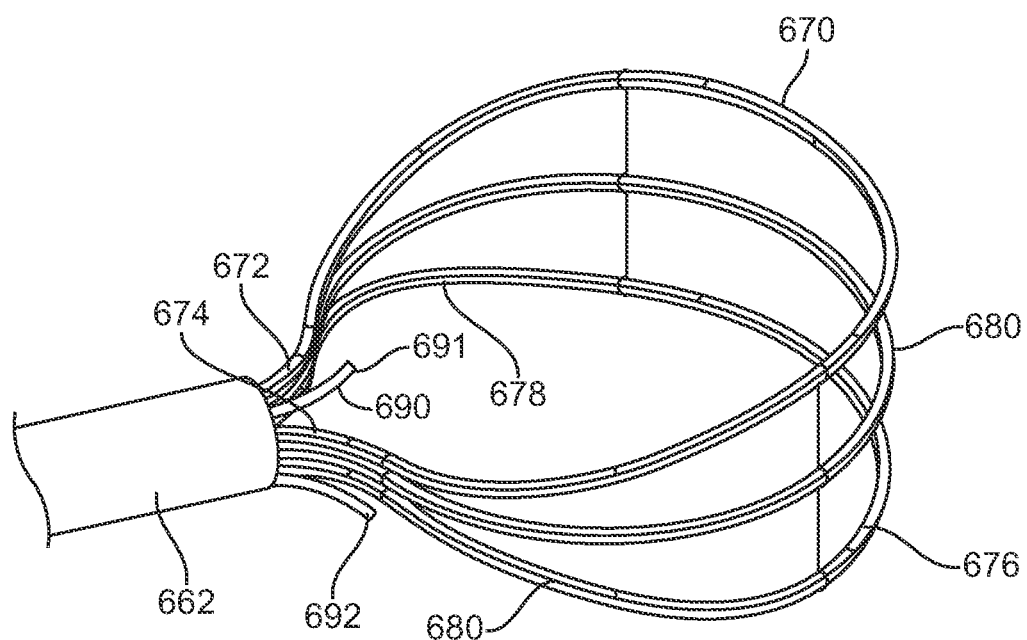
FIG. 8B shows the tissue manipulator expanded with filaments extending between loops.
Figure 8C:
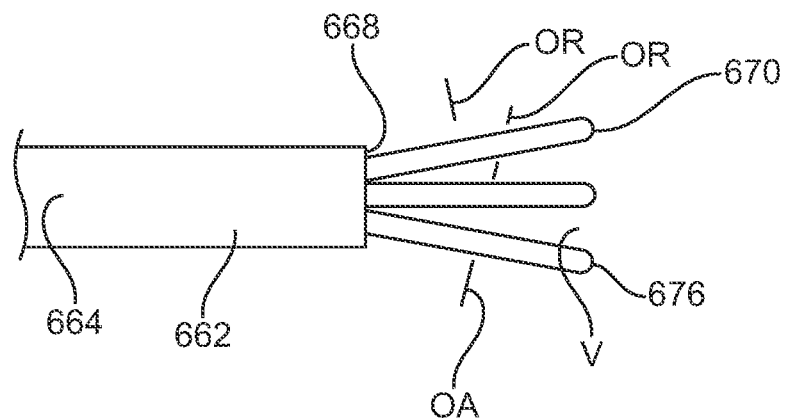
FIG. 8C shows another view of the loops with the filaments removed.
Figure 9:
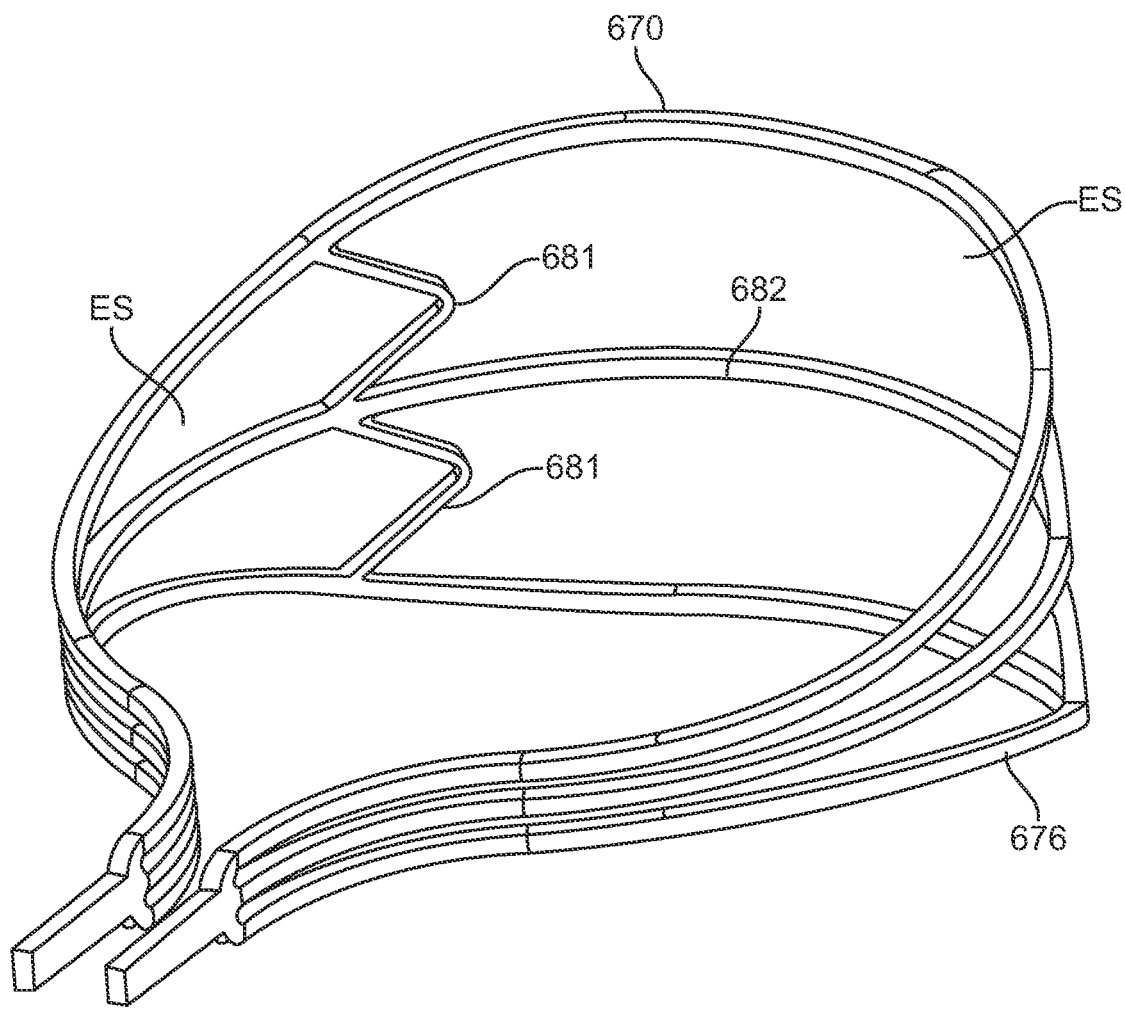
FIG. 9 shows another tissue manipulator with integrally formed intermediate elements.
Figure 10:
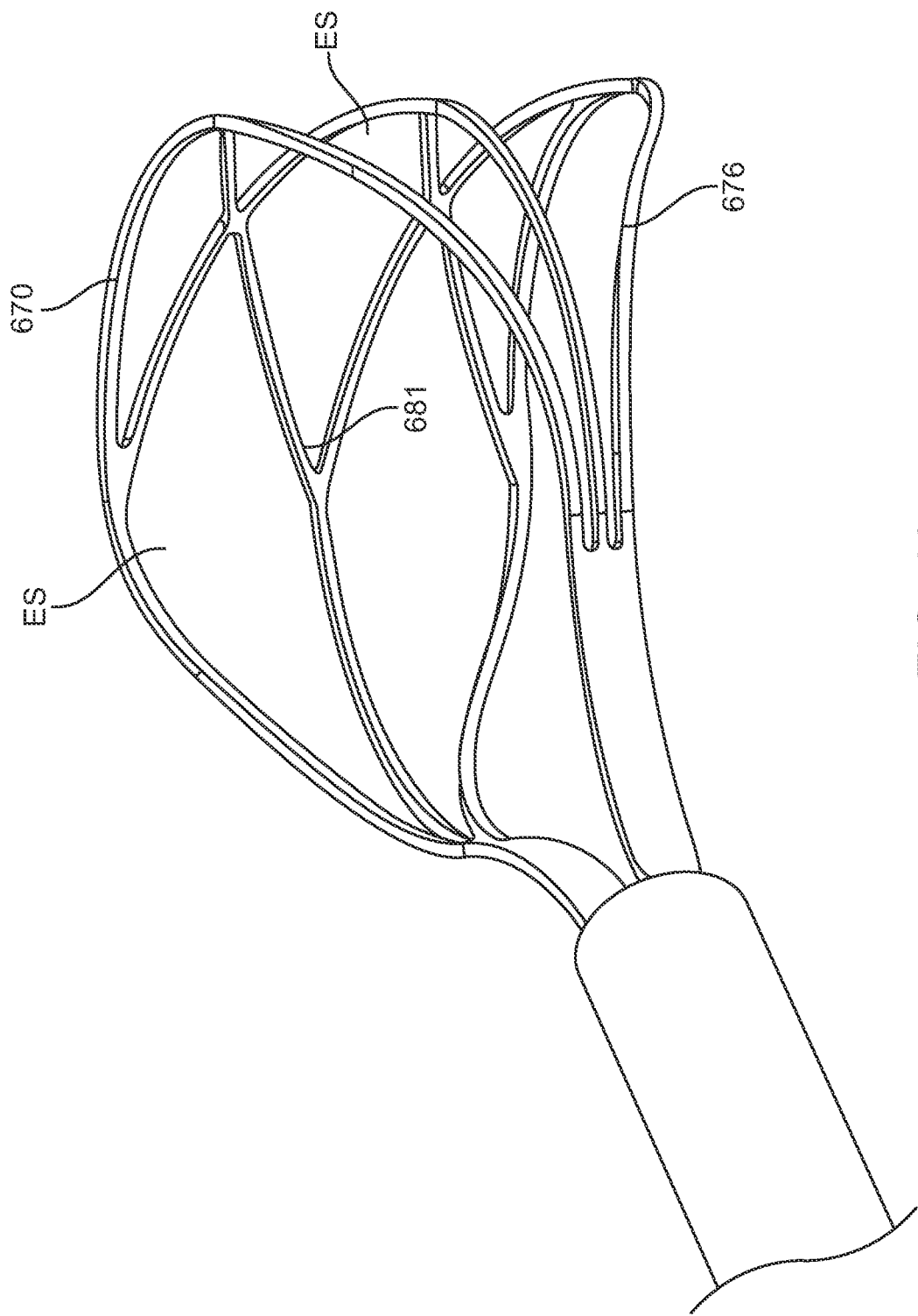
FIG. 10 shows another tissue manipulator with integrally formed intermediate elements.

The tissue manipulator 660 may also include an intermediate element 680 positioned between the first loop 670 and the second loop 676. The intermediate element 680 may be a third loop 682 positioned between the first loop 670 and the second loop 676. The intermediate element 680 may include an interconnecting element 682 extending between the first loop 670 and the second loop 676. The interconnecting element 682 may be integrally formed elements 681 with the first loop and the second loop as shown in FIGS. 9 and 10. Alternatively, the interconnecting element may be a flexible filament 684 extending between the first loop and the second loop as shown in FIG. 8B. The third loop 682 may have the features of the first and second loops. The orientation OA which maximizes an area of the third loop may be within 30 degrees of perpendicular to the longitudinal axis LA.

The first and second loops provide a controlled amount of exposed surface therebetween to control, and optionally cut, a controlled amount of the material. The exposed surface ES between the first loop 670 and the second loop 676 has an area of 15 mm(2) to 60 mm(2). Stated another way, the exposed surface between the first loop and the second loop is 3-10 times the effective diameter in the expanded position (or the unbiased position since they may be the same).

The exposed surface between the first loop and the second loop may have 2-8, 2-6, 2-4 or even just 2 independent cells when viewed in a radially inward direction relative to the orientation axis of the first and second loops 670, 676. The exposed surface ES has an area which is at least 4 times larger than an area of the intermediate element 680 positioned between the first loop and the second loop 670, 676 when the exposed surface ES is viewed radially inward with respect to the first and second loops 670, 676. In this manner, the intermediate element 680 does not take up an excessive amount of room as compared to some net-type devices.

The first loop 670 may also be formed so that at least 80% of the loop is 1.5-3.5 mm from the second loop 676. The first and second loops 670, 676 (and optional intermediate element) may also be configured to cut material contained within therein when collapsed. A source of suction may be coupled to the lumen with suction being used together with or separately from the tissue manipulator. Irrigation may also be supplied with the other shafts incorporated herein and such incorporation is expressly provided here.

The device 660 may include a first support element 690 extending from a distal end of the shaft when the first loop 670 is in the expanded position. The first support element 690 may be an elongate element that extends to a free end 691. The first support element 690 is positioned with the free end 691 positioned within an area of the first loop 670 when viewing the first loop along the orientation OA that maximizes the area of the first loop 670. The first loop 670 has an effective diameter when in the expanded position while the first support element 690 extends into the area of the first loop so that the free end is positioned 0.05 to 0.30 times the effective diameter of the first loop within the first loop 670 when viewed along the orientation OA. A second support element 692 cooperating with the second loop 676 in the same manner may also be provided.

Figure 11:
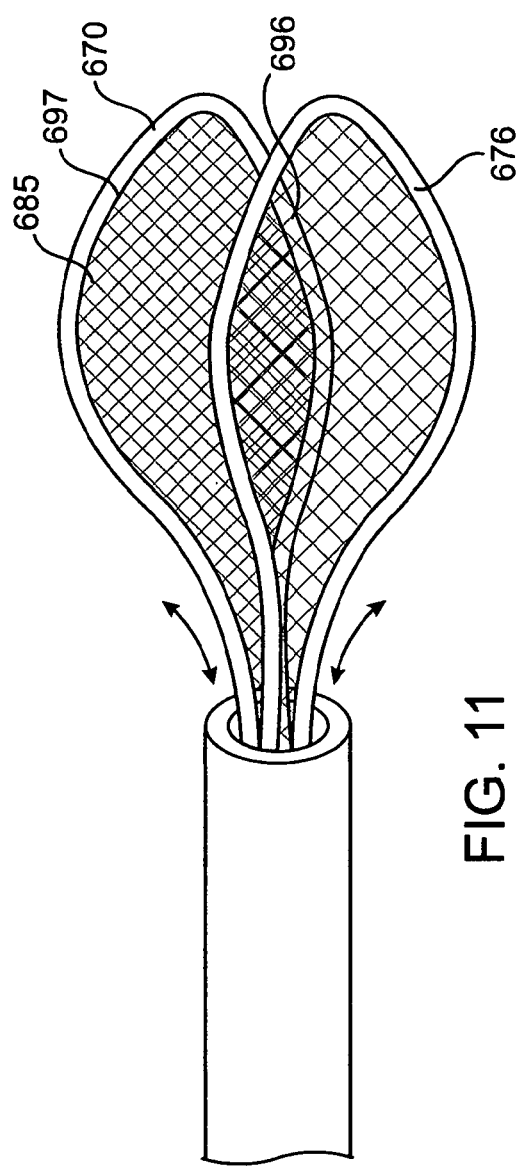
FIG. 11 shows still another tissue manipulator with a net-like material within the loops.

Referring to FIG. 11, the first loop and/or second loop may have at least one interconnecting element 695 extending from a first connection 696 to the loop to a second connection 697 on the same loop or the loop(s) may be substantially free of any such interconnecting elements depending upon the desired use. For example, a net-like material as shown in FIG. 11 may be provided or the loops may be free of interconnecting elements so that the open area is free. All discussion and limitation of the first loop are applicable to the first loop, the second loop and the third loop as well as discussion of the first support applicable to the second support. The first support may extend independently or simultaneously with the first loop. The first support helps to secure material within the first loop by extending into the opening area formed by the loop.

The first and second legs of the first and second loop(s) may be movable within the lumen. Alternatively, the first leg and the second leg of the first loop are coupled to an actuator extending through the lumen so that movement of the actuator moves the first leg and the second leg between the collapsed position and the expanded position. The first leg and the second leg of the second loop are coupled to an actuator extending through the lumen so that movement of the actuator moves the first leg and the second leg between the collapsed position and the expanded position. The first loop and/or the second loop may be positioned entirely distal to the distal opening in the expanded position. The first loop and the second loop may include a superelastic material within a superelastic range when in the collapsed position.

Figure 12:
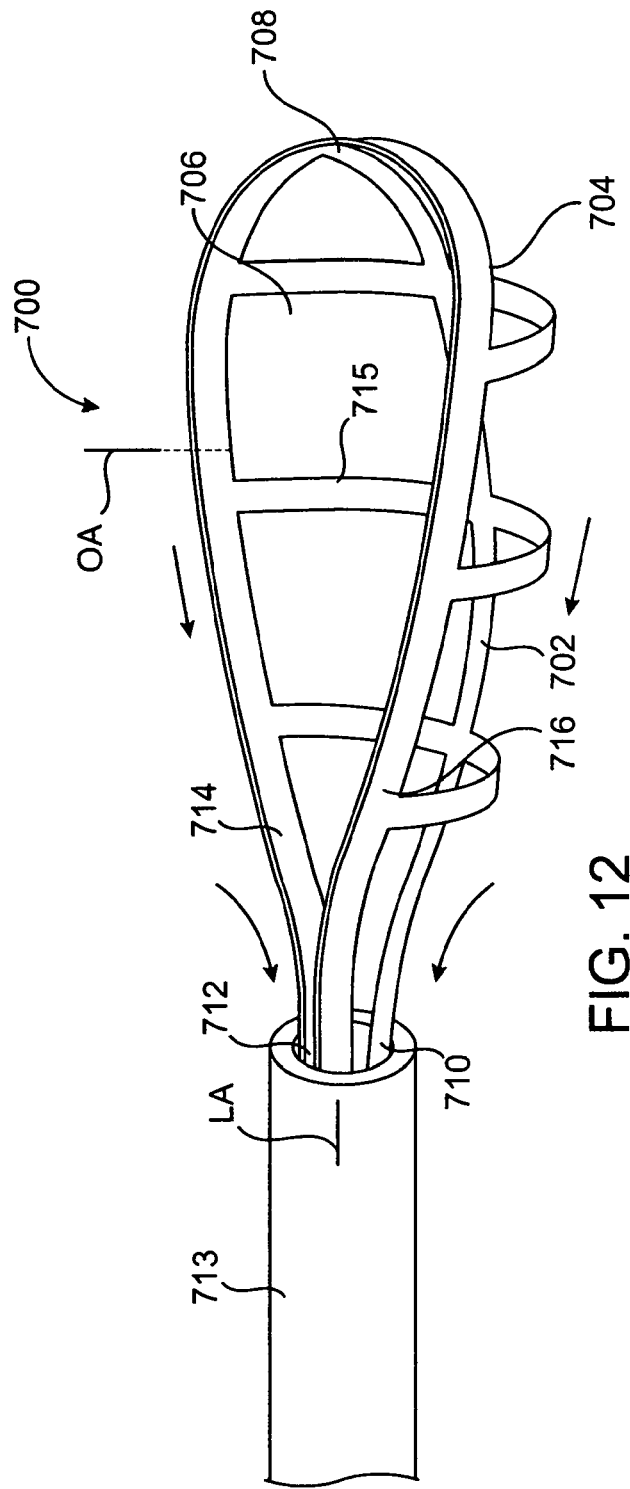
FIG. 12 shows still another tissue manipulator having a loop with an integrally formed concave element.

Referring to FIG. 12, a tissue manipulator 700 has a concave element 702 coupled to a first loop 704 to form a basket 706 to receive material. The concave element 702 may have one end 708 integrally formed with the first loop 704 with the other end 710 movable within a lumen 712 of a shaft 713 independent of a first leg 714 and a second leg 716 of the first loop 704. Cross-elements 715 are also integrally formed with the first loop 704 and may also be integrally formed with the concave element 702. Alternatively, both ends 708, 710 may be integrally formed with the loop 704.

Figure 13:
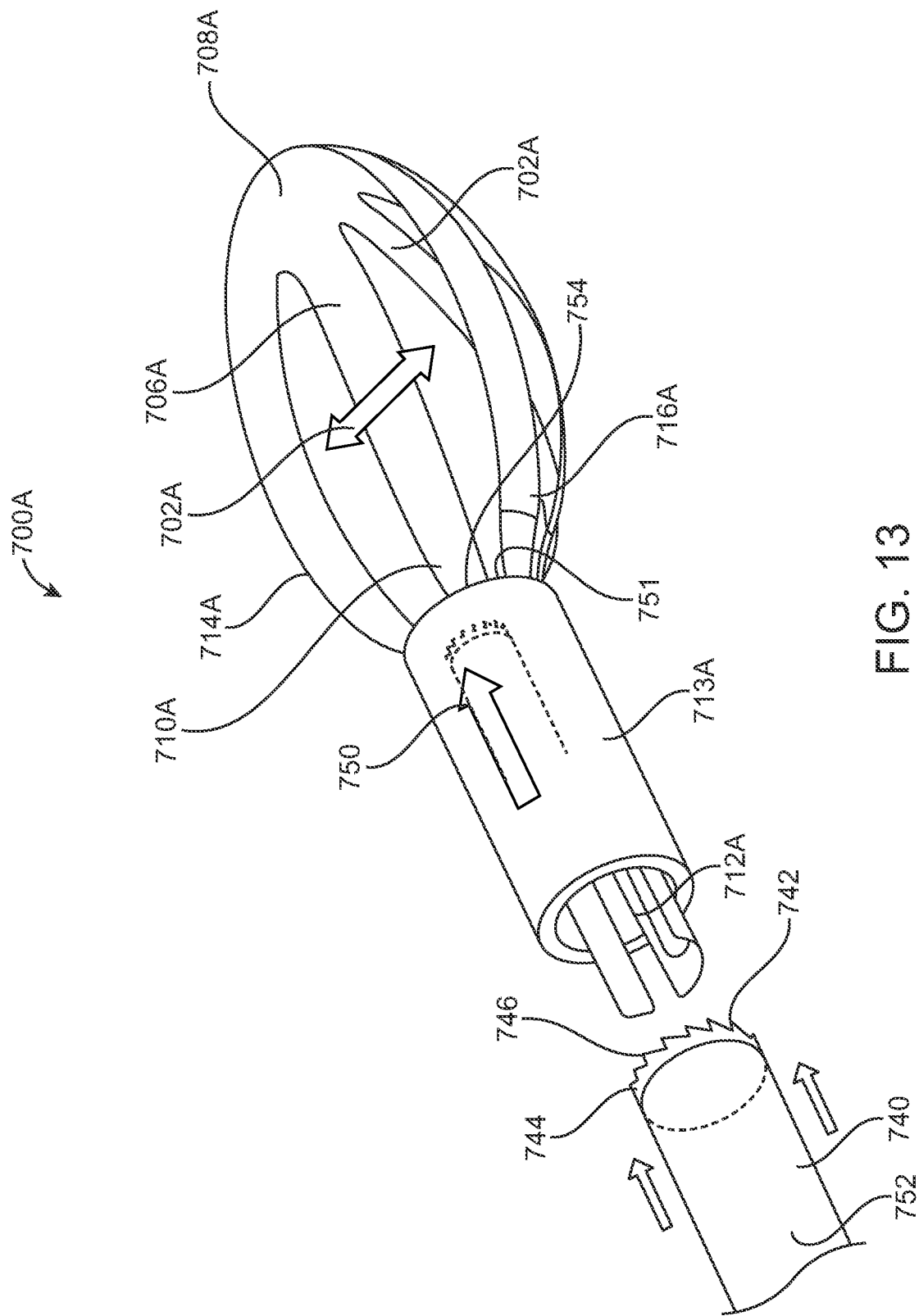
FIG. 13 shows still another tissue manipulator with a rotating cutter.
Figure 14:
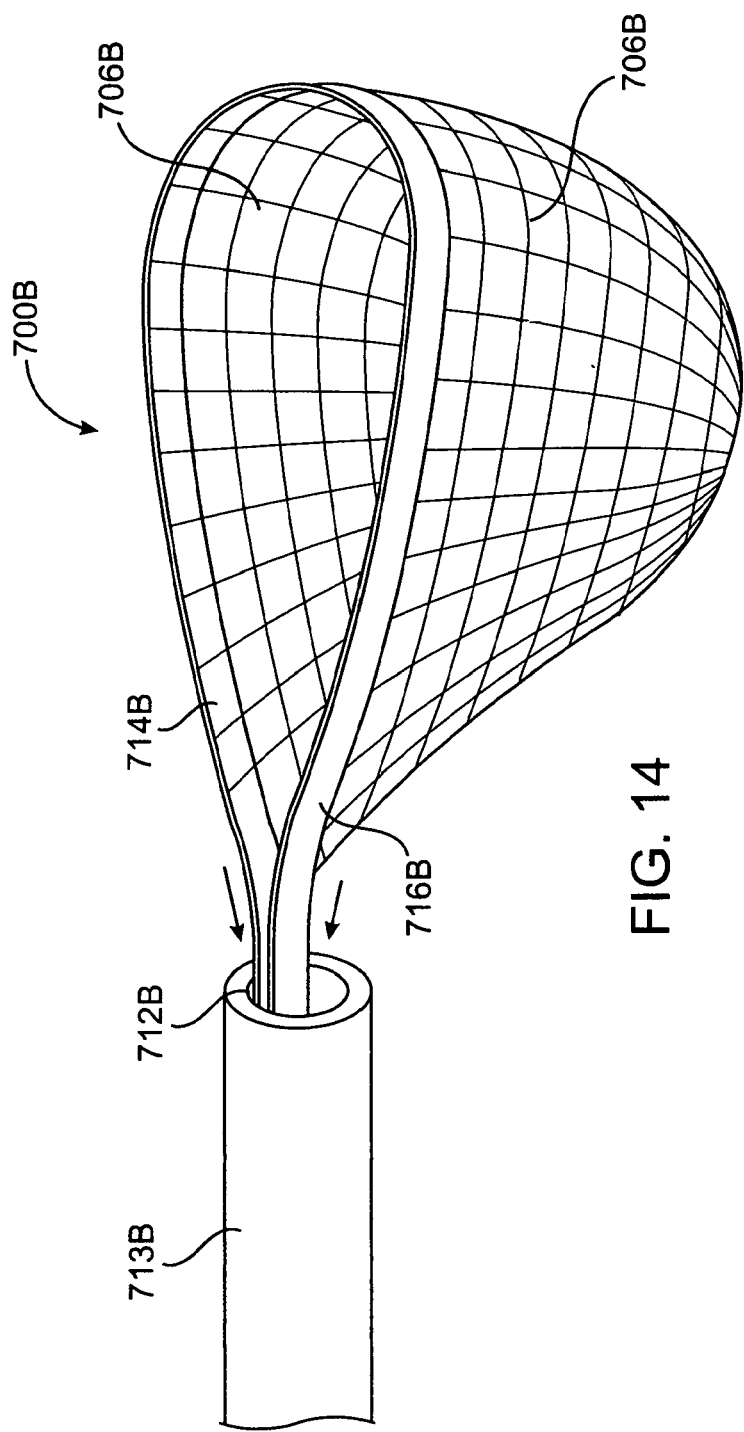
FIG. 14 shows another tissue manipulator with a net-like material.

Another tissue manipulator 700A is shown in FIG. 13 wherein the same reference numbers refer to the same or similar structure. A concave element 702A, which may be 2-3 concave elements 702A. The manipulator 700A has a first loop 704A with a first leg 714A and second leg 716A. A first end 708a of the concave element 702A may be integrally formed with the loop 704A while the second end 710A may be independently movable within a lumen 712A. The loop 704A and the concave element 702A may be made of ribbon-shaped material having a width to thickness ratio of more than 3 to 1 to create a more closed basket 706A compared to wire having a 1 to 1 ratio. Referring to FIG. 14, another tissue manipulator 700B is shown wherein the same or similar reference number refer to the same or similar structure. The manipulator 700B has a first loop 704B with a concave element 702B being a net 703. The net 703 may be integrally formed or a separate element attached to the loop 704B.

Figure 15:
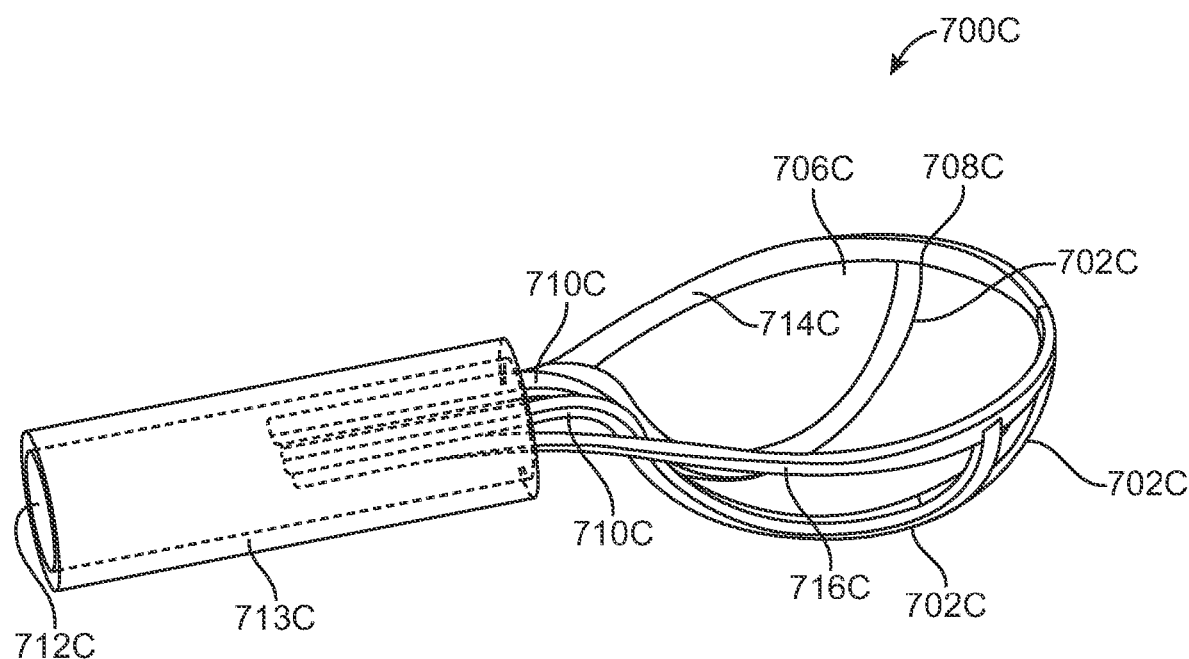
FIG. 15 shows still another tissue manipulator.

Referring to FIG. 15, another tissue manipulator 700C is shown wherein the same or similar reference number refer to the same or similar structure. The manipulator 700C has a first loop 704C with a concave element 702C, which may be 2-3 concave elements 702C, integrally formed at first end 708C and may have a second end 710C independently movable within a lumen 712C within shaft 713C, or a separate element attached to the loop 704B. The manipulator 700C is free of interconnecting elements between any two sides of the loop and may also include no interconnecting elements between the concave elements 702C.

Figure 16:
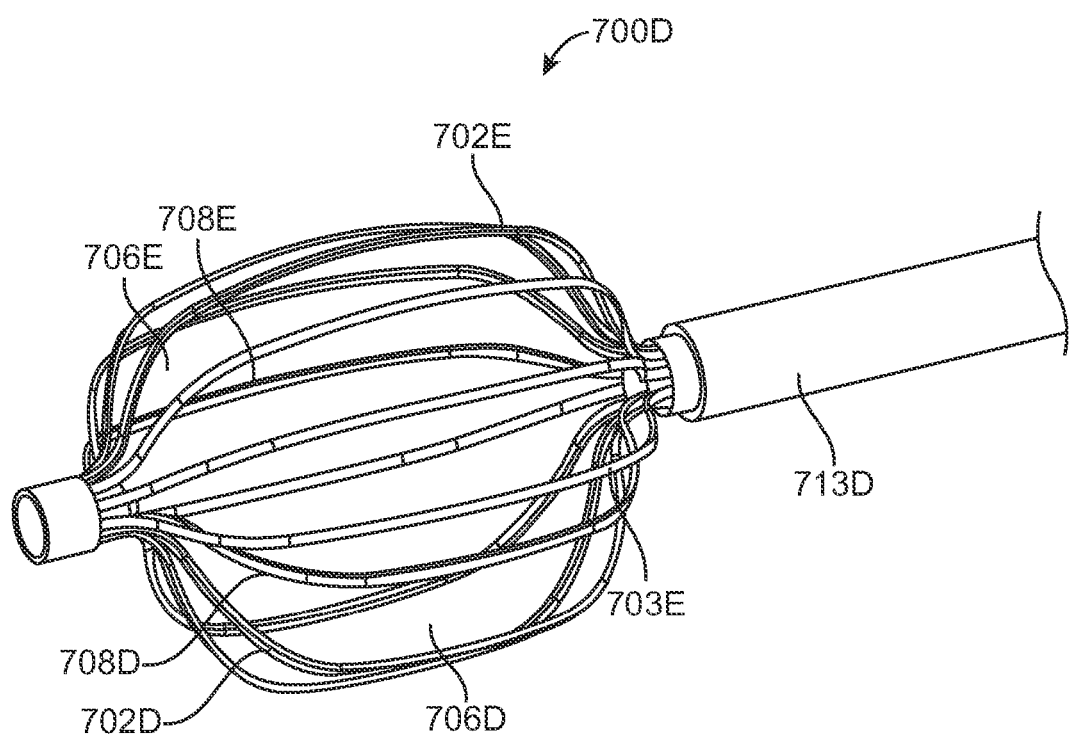
FIG. 16 shows a tissue manipulator having two opposing baskets.
Figure 17:
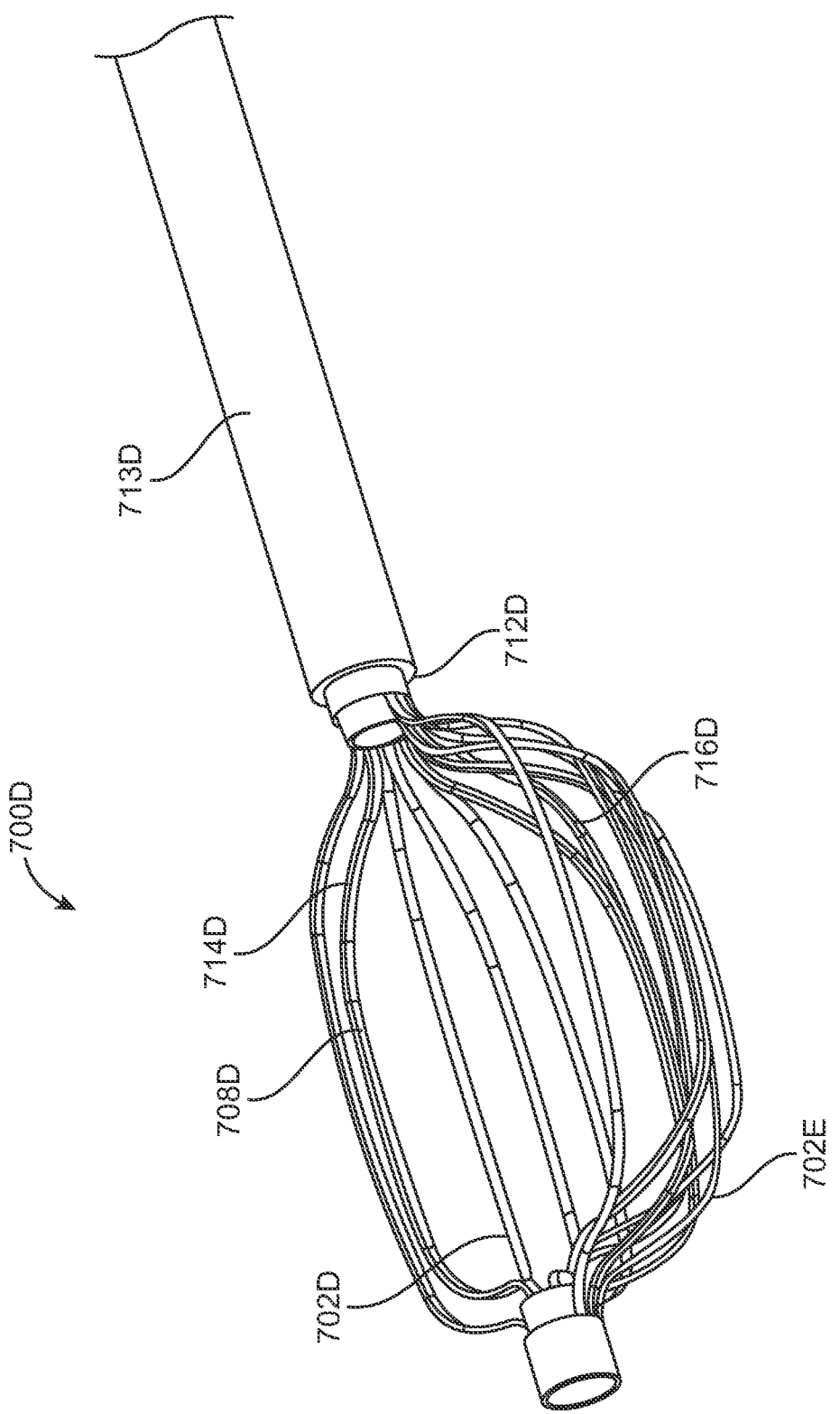
FIG. 17 shows the opposing baskets in a nested position.

Referring to FIGS. 16 and 17, another tissue manipulator 700D is shown in FIG. 16 wherein the same reference numbers refer to the same or similar structure. The tissue manipulator 700D has a first loop 708D and a second loop 708E with corresponding concave elements 708D and 708E, respectively. A first basket 706D and a second basket 706E are movable between a nested position of FIG. 17 and a position in which the two baskets oppose one another as shown in FIG. 16.

Referring to FIG. 12 again, the tissue manipulator 700 is described further and it is understood that all aspects described here are applicable to all of the other tissue manipulators 700A-D and are expressly incorporated for each. The loop 704 has an unbiased shape which bounds an area defined in an orientation OA that maximizes the area. The area has an effective diameter which is equal to the diameter of a circle having the same area. The first loop 704 moves toward the unbiased shape when moving from the collapsed position to the expanded position. The first loop 704 may have effective diameter of 4.5 mm to 6.5 mm or 5.0 mm to 6.0 mm. Of course, the various aspects of the invention may be carried out with different sizes. As used herein, the "area" of the loop is determined by the orientation OA which maximizes the area. The first loop is expanded with the first loop orientation being within 45 degrees of perpendicular to a longitudinal axis LA at a distal end of the shaft 713.

Referring again to FIG. 13, a rotating cutter 740 is shown which may be used with any of the device and methods described herein. The rotating cutter 740 has a cutting element 742 at a distal end 744 which may be a series of teeth 746, a sharpened edge, ridges spikes or any other suitable shape. Rotating as used herein may mean rotation in one direction and then back in the other without departing from the scope of the invention. The rotating cutter 740 may be independently positioned and moved for use as desired or may be fixed in a working position shown by dotted-line working position 750. The rotating cutter 740 is recessed from the distal end 751 of the shaft 713A when in the working position 750 so that the rotating cutter 740 is not exposed from an opening 754 at the distal end 744. The tissue manipulating devices of the present invention may be used to push, draw, squeeze or otherwise manipulate tissue into engagement with the rotating cutter 740. The rotating cutter 740 may further have a suction lumen 752 therein for suctioning material.

Referring now to FIGS. 18A-18D and 19, a cutting device 800 for cutting material in the eye and, in a specific application, for cutting a whole lens while contained within a capsular bag is shown. The cutting device 800 has a shaft 802 with a first shaft part 804 and a second shaft part 806 which are movable relative to one another between a first position of FIG. 18A and a second position of FIG. 19. An elongate element 808 has a first end 810 coupled to the first shaft part 804 and a second end 812 coupled to the second shaft part 806. The cutting device 800 forms a loop 814 with at least part of the elongate element 808 forming the loop 814 together with the shaft 802. The loop 814 moves from a collapsed position of FIG. 18A to an expanded position of FIG. 19 when the first and second shaft parts 804, 806 move from the first position to the second position. The loop 814 may be expanded to advance the loop 814 between the capsular bag and the whole lens. Material is positioned in an open area 813 of the loop 814 and then cut by collapsing the loop 804.

Figure 18A:
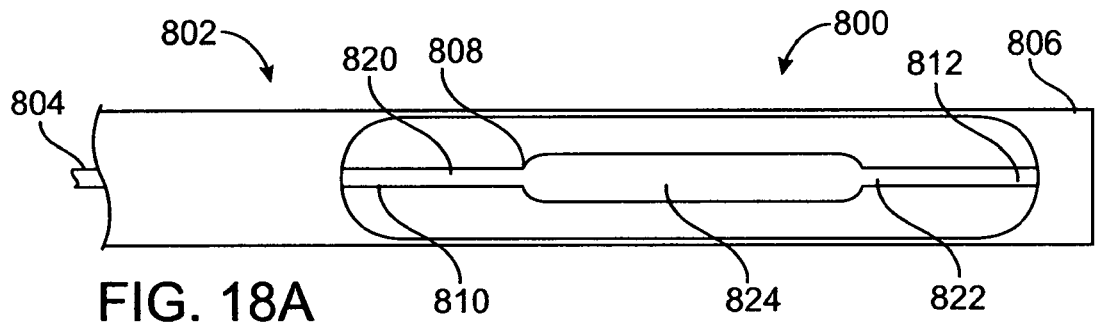
FIG. 18A shows a device for cutting material within the eye.
Figure 18B:
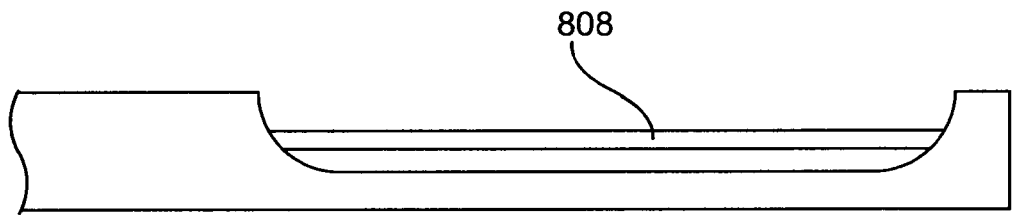
FIG. 18B shows a side view of the device of FIG. 19A.
Figure 18C:
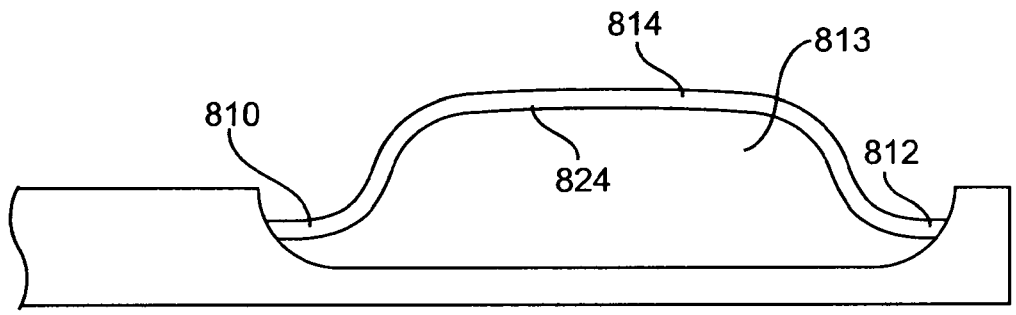
FIG. 18C shows the device of FIG. 19A with an elongate element deformed to expand a loop formed by the device.
Figure 18D:
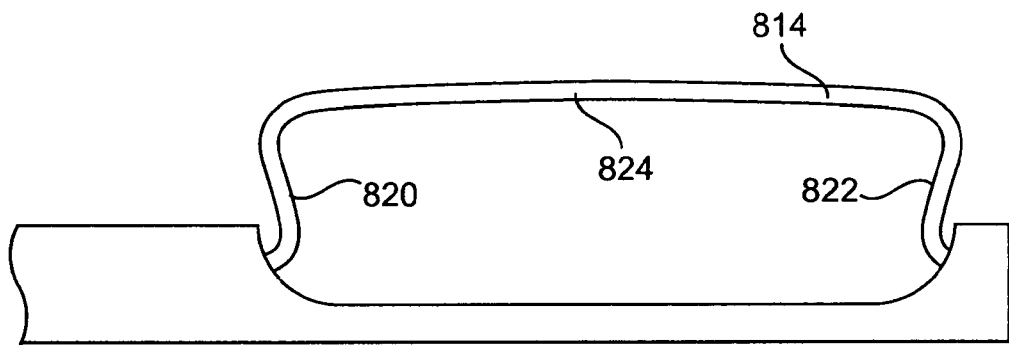
FIG. 18D shows the device of FIG. 19C further expanded.

The elongate element 808 expands in a manner which facilitates cutting the whole lens within the capsular bag. The elongate element 808 may have a first flexible portion 820 and optionally a second flexible portion 822 with an intermediate portion 824 therebetween. The elongate element 808 initially expands laterally outward as shown in FIG. 18C. When the first and second flexible portions 820, 822 begin to bend, the loop 814 has a proximal portion 826 and a distal portion 828 which extend proximally and distally, respectively, from the intermediate portion 824. The flexible portion may be at least 1.5 more stiff in bending than the intermediate portion. Furthermore, the elongate element 808 may be in an unbiased position when collapsed as shown in FIG. 18A with the elongate element 808 being deformed to deflect and expand the loop. Of course, the elongate element 808 may also have a preset shape which facilitates movement to the expanded position while requiring less force to deform the elongate element 808.

Figure 19:
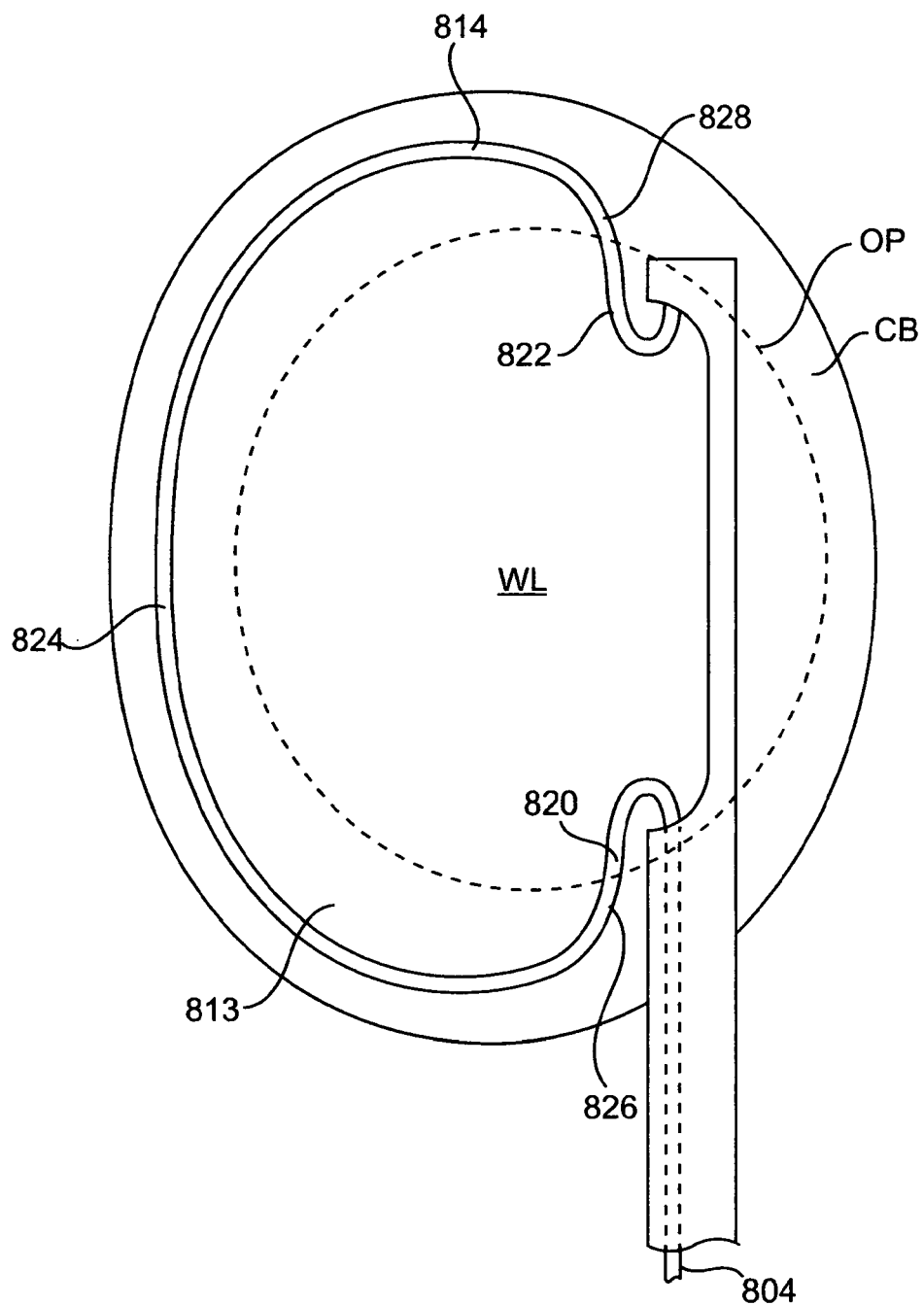
FIG. 19 shows the device of FIG. 19A-D full expanded and positioned within a capsular bag and advanced between the capsular bag and the lens when the loop is expanded.
Figure 20A:
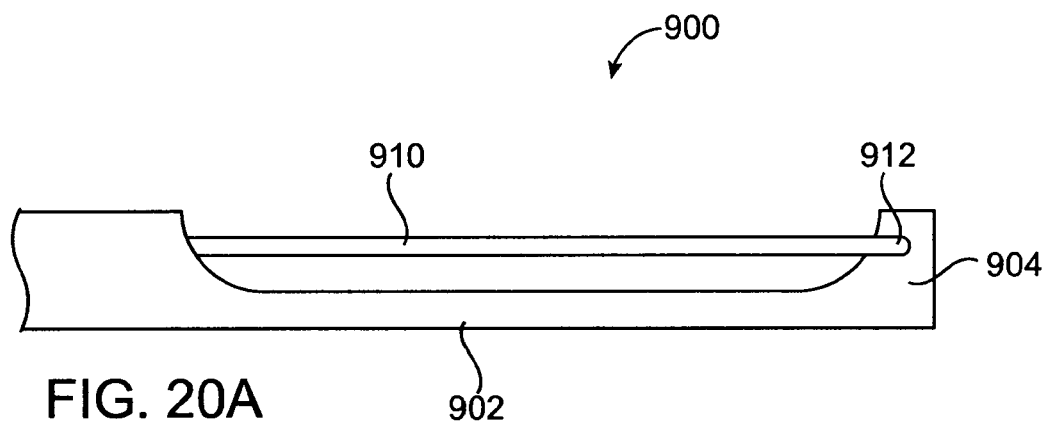
FIG. 20A shows another cutting device in a collapsed position.
Figure 20B:
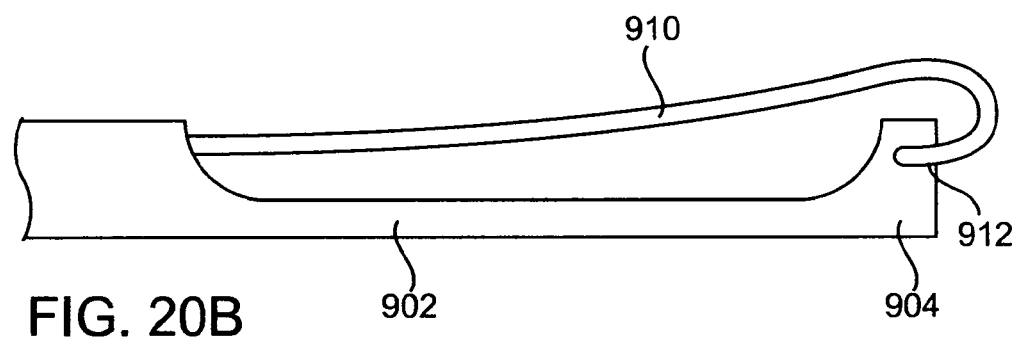
FIG. 20B shows the device of FIG. 21A partially expanded with the distal end changing orientation with respect to the proximal end of the shaft.
Figure 20C:
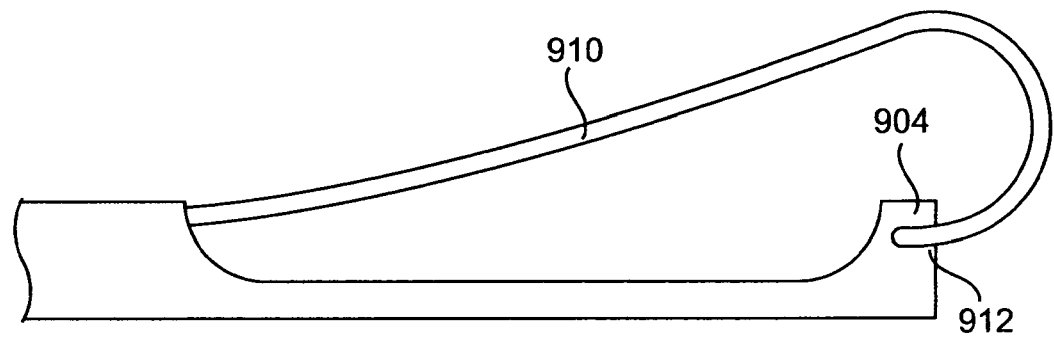
FIG. 20C shows a loop formed by the device advancing distally.

Referring now to FIGS. 20A-C and 21A-B, another cutting device 900 is shown for cutting material in the eye and, in a specific application, for cutting a whole lens WL within a capsular bag CB through an opening OP (such as a capsulorhexis) that exposes an anterior surface of the lens (see FIG. 19). A shaft 902 has a first shaft part 904 and a second shaft part 906 movable relative to one another between the position of FIG. 20A and FIG. 21B so that a loop 908 formed by the device 902 moves from a collapsed position to an expanded position. An elongate element 910 has a first end 912 coupled to the first shaft part 904 and a second end 914 coupled to the second shaft part 906. The loop 908 is formed at least in part by the elongate element 910 with the loop 908 also being formed by a portion of the shaft 902.

Figure 21A:
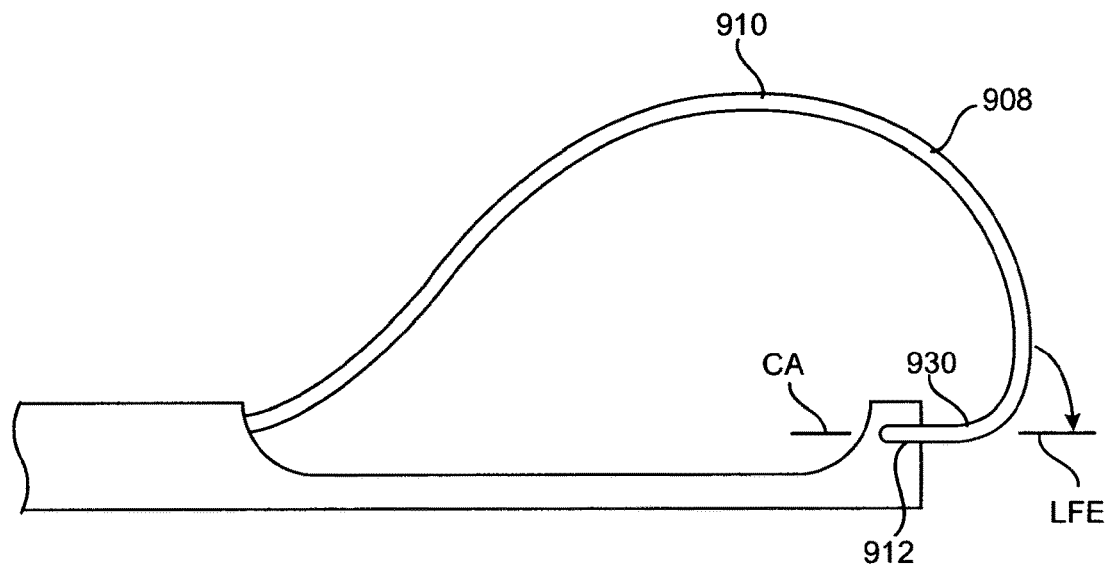
FIG. 21A shows the loop expanded further.
Figure 21B:
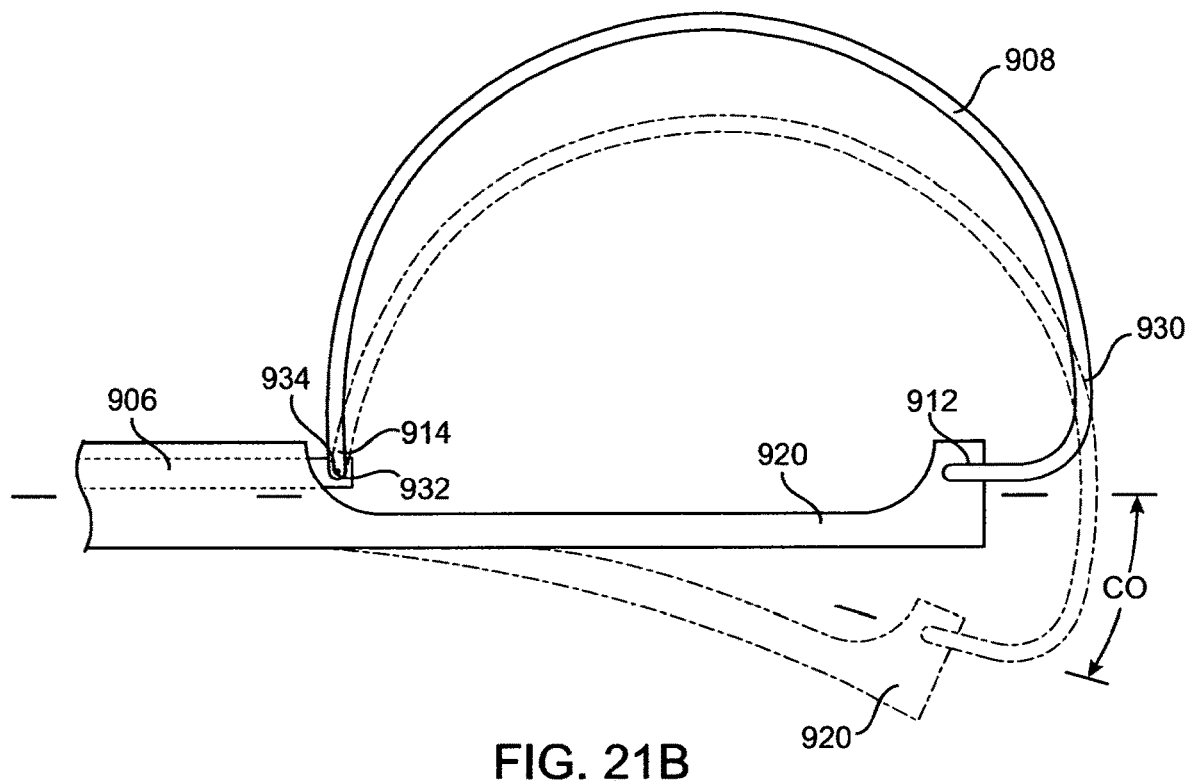
FIG. 21B shows the loop expanded with the proximal end of the elongate element also changing orientation with respect to the shaft.

The loop 908 is expanded so that the first end 912 has a longitudinal orientation LFE that changes by an angle CA at least 120 degrees with respect to the shaft 902 adjacent to the second end 914 of the elongate element 910 when the first and second shaft parts 904, 906 move from the first position to the second position. FIG. 21A shows the angle CA being about 180 degrees.

The 902 shaft may also include a flexible distal end 920 with the first end 912 of the elongate element 910 coupled to the flexible distal end 920 of the shaft 902. The flexible distal end 920 of the shaft 902 may contribute to the changing orientation of the first end 912 with respect to the longitudinal orientation of the shaft 902 adjacent the second end 914. The flexible distal end 920 may change in orientation by an angle CO of at least 30 degrees when the first and second shaft parts move from the first position to the second position.

The first end 912 of the elongate element 912 may be have a pinned connection so that the first end 912 rotates relative to the first shaft part 904 for an angle of at least 120 degrees and may be for 180 degrees+/−45 degrees when the first and second shaft parts move from the first position to the second position. The loop 908 has a distal portion 930 that advances distally beyond a distal end of the shaft 902 as the loop 908 moves from the collapsed position to the expanded position. The first end 912 of the elongate element changes orientation so that the loop 908 advances distally beyond a distal end of the shaft 902 as the loop 908 moves from the collapsed position to the expanded position. The second end 914 may also have a rotatable connection 932, such as a pinned connection 934, to the second shaft part 906. The second end 914 may rotate and change in orientation relative to the shaft adjacent the second end by 90 degrees+/−45 degrees when the first and second shaft parts 904, 906 move from the first position to the second position. The elongate element 912 may be in an unbiased position in FIG. 20A with the elongate element 912 deformed into the positions of FIG. 21A and FIG. 21B. Of course, the elongate element 912 may also have a preset shape similar to FIG. 21B without departing from the scope of the invention.

Use of and discussion of all aspects of the first flexible portion or the first end are equally applicable to the second end and are specifically incorporated herein. Furthermore, a mixture of first end and second end are also expressly incorporated such as a flexible first end and a rotatable second end or the reverse. The elongate element may be without a preset shape although numerous aspects of the present invention may be practiced with a wholly or partially preset shape. The elongate element may not include a superelastic material in this and other embodiments which may reduce the cost of the device. The loop moves from an unbiased position toward a biased position, and an increasing the bias or load on the elongate element, when moving from the collapsed position to the expanded position.

Use of the terms "first" and "second" are used with reference to each specific application, however, the terms are interchangeable and, thus, the claims may define an aspect as the "second" even though it is described as the "first" elsewhere without departing from the scope of the invention. For example, the terms first and second may simply be interchanged. In another example, the "first" may be omitted so that the "second" becomes the "first."

Although embodiments of various methods and devices are described herein in detail with reference to certain versions, it should be appreciated that other versions, embodiments, methods of use, and combinations thereof are also possible within the scope of the invention. Therefore, the spirit and scope of the invention should not be limited to the description of the embodiments contained herein. Furthermore, although the various embodiments and description may specify certain anatomical locations, species, or surgical procedures, it should be appreciated that these embodiments apply to other locations, species, and surgical procedures. For example, the device may include a remote suction source while still providing for purging of the suction path. The device also includes no powered elements but a pneumatic source of power (pressurized canister) or a battery may be used without departing from numerous aspects of the present invention. Thus, as it can be seen, the invention has been described with respect to various independent aspects.

What is claimed is:

1. An ophthalmic surgical device for cutting a lens while the lens is contained within a capsular bag of a human eye, the device comprising:
   an elongate shaft defining a longitudinal axis, the elongate shaft comprising a lumen, an opening from the lumen, and a distal-most end, wherein the opening extends through a side wall of the elongate shaft near the distal-most end; and
   a sectioning element operably coupled to the elongate shaft and comprising a looped segment configured to transition between a collapsed, insertion configuration and a fully expanded, capture configuration,
   wherein transition of the looped segment from the collapsed, insertion configuration towards the fully expanded, capture configuration causes the looped segment to exit the lumen through the opening and causes a proximal portion of the looped segment to move proximally relative to the opening and a distal portion of the looped segment to move distally relative to the opening, and
   wherein, when the looped segment is in the fully expanded, capture configuration, the looped segment defines, in part, an open area sized and shaped to receive the lens of the human eye, the proximal portion of the looped segment overlapping a first portion of the side wall that is located proximal to the opening and the distal portion of the looped segment overlapping a second portion of the side wall that is located distal to the opening and is located distal to the distal-most end of the elongate shaft,
   wherein transitioning the looped segment from the fully expanded, capture configuration towards the collapsed, insertion configuration is configured to cut the lens positioned within the open area.

2. The device of claim 1, wherein the elongate shaft comprises a first shaft part and a second shaft part, wherein the sectioning element has a first end coupled to the first shaft part and a second end coupled to the second shaft part.

3. The device of claim 2, wherein the looped segment transitions towards the fully expanded, capture configuration when the first and second shaft parts move from a first position to a second position.

4. The device of claim 1, wherein the looped segment advances between the capsular bag and the lens as the looped segment is transitioned towards the fully expanded, capture configuration.

5. The device of claim 1, wherein the looped segment comprises a first flexible portion, a second flexible portion, and an intermediate portion located between the first and second flexible portions.

6. The device of claim 5, wherein the intermediate portion of the looped segment moves laterally outward through the opening during transition towards the fully expanded, capture configuration.

7. The device of claim 6, wherein the first and second flexible portions of the looped segment are stiffer than the intermediate portion.

8. The device of claim 1, wherein the sectioning element is unbiased when in the collapsed, insertion configuration.

9. The device of claim 1, wherein the sectioning element has a preset shape and is unbiased when in the fully expanded, capture configuration.

10. The device of claim 1, wherein the sectioning element comprises a superelastic wire.

11. The device of claim 1, wherein the elongate shaft and the sectioning element when the looped segment is in the collapsed, insertion configuration are dimensioned for passage through an incision in the cornea via an ab interno approach.

* * * * *